US007608433B2

(12) United States Patent
Hoffmann et al.

(10) Patent No.: US 7,608,433 B2
(45) Date of Patent: Oct. 27, 2009

(54) METHOD OF DETECTION OF CLASSICAL SWINE FEVER

(75) Inventors: Bernd Hoffmann, Liepgarten (DE); Klaus Depner, Neuenkirchen (DE); Martin Beer, Neuenkirchen (DE)

(73) Assignee: Idexx Laboratories, Westbrook, ME (US)

( * ) Notice: Subject to any disclaimer, the term of this patent is extended or adjusted under 35 U.S.C. 154(b) by 395 days.

(21) Appl. No.: 11/052,762

(22) Filed: Feb. 9, 2005

(65) Prior Publication Data

US 2006/0177818 A1 Aug. 10, 2006

(51) Int. Cl.
*C12P 19/34* (2006.01)
*C12Q 1/68* (2006.01)
*C07H 21/02* (2006.01)
*C07H 21/04* (2006.01)

(52) U.S. Cl. ......................... 435/91.2; 435/6; 536/23.1; 536/24.3; 536/24.33

(58) Field of Classification Search ....................... None
See application file for complete search history.

(56) References Cited

U.S. PATENT DOCUMENTS

| | | | | |
|---|---|---|---|---|
| 4,415,732 | A | 11/1983 | Caruthers et al. | 536/26.5 |
| 4,458,066 | A | 7/1984 | Caruthers et al. | 536/25.34 |
| 4,500,707 | A | 2/1985 | Caruthers et al. | 536/25.34 |
| 4,659,774 | A | 4/1987 | Webb et al. | 525/54.2 |
| 4,725,677 | A | 2/1988 | Koster et al. | 536/25.34 |
| 4,786,724 | A | 11/1988 | Letsinger | 536/25.6 |
| 4,923,901 | A | 5/1990 | Koester et al. | 521/53 |
| 4,980,460 | A | 12/1990 | Molko et al. | 536/26.71 |
| 5,047,524 | A | 9/1991 | Andrus et al. | 536/25.31 |
| 5,071,974 | A | 12/1991 | Groody | 536/25.34 |
| 5,112,962 | A | 5/1992 | Letsinger et al. | 536/25.3 |
| 5,164,491 | A | 11/1992 | Froehler et al. | 536/26.3 |
| 5,175,209 | A | 12/1992 | Beattie et al. | 525/54.11 |
| 5,198,527 | A | 3/1993 | Marks et al. | 528/198 |
| 5,204,455 | A | 4/1993 | Froehler et al. | 536/22.1 |
| 5,204,456 | A | 4/1993 | Molko et al. | 536/25.33 |
| 5,218,103 | A | 6/1993 | Caruthers et al. | 536/25.33 |
| 5,243,038 | A | 9/1993 | Ferrari et al. | 536/23.1 |
| 5,262,530 | A | 11/1993 | Andrus et al. | 536/25.31 |
| 5,278,302 | A | 1/1994 | Caruthers et al. | 536/24.5 |
| 5,281,701 | A | 1/1994 | Vinayak | 536/25.34 |
| 5,348,868 | A | 9/1994 | Reddy et al. | 435/91.1 |
| 5,380,833 | A | 1/1995 | Urdea | 536/22.1 |
| 5,391,667 | A | 2/1995 | Dellinger | 526/264 |
| 5,391,723 | A | 2/1995 | Priest | 536/23.1 |
| 5,419,966 | A | 5/1995 | Reed et al. | 428/406 |
| 5,446,137 | A | 8/1995 | Maag et al. | 536/23.1 |
| 5,453,496 | A | 9/1995 | Caruthers et al. | 536/24.5 |
| 5,476,925 | A | 12/1995 | Letsinger et al. | 536/23.1 |

FOREIGN PATENT DOCUMENTS

| | | |
|---|---|---|
| WO | WO 94/17810 | 8/1994 |
| WO | WO 94/23744 | 10/1994 |

OTHER PUBLICATIONS

Klerks M.M. et al 'Comparison of real-time PCR methods for detection of *Salmonella enterica* and *Escherichia coli* O157:H7, and introduction of a general internal amplification control.' J Microbiol Methods. Dec. 2004;59(3):337-49.*

Risatti G.R. et al 'Rapid detection of classical swine fever virus by a portable real-time reverse transcriptase PCR assay.' J Clin Microbiol. Jan. 2003;41(1):500-5.*

Fratamico, P.M., Deng, M.Y., Strobaugh, T.P., and Palumbo, S.A. 1997. Construction and characterization of *Escherichia coli* O157:H7 strains expressing firefly luciferase and green fluorescent protein and their use in survival studies. J. Food Prot.*

Wirz B. et al 'Detection of hog cholera virus and differentiation from other pestiviruses by polymerase chain reaction.' J Clin Microbiol. May 1993;31(5):1148-54.*

Definition of 'derive' from www.yourdictionary.com/derive, accessed on Apr. 3, 2008, pp. 1-3.*

Klein D et al 'Accurate estimation of transduction efficiency necessitates a multiplex real-time PCR.' Gene Therapy (2000) 7, 458-463.*

Cook R.F. et al. 'Development of a multiplex real-time reverse transcriptase-polymerase chain reaction for equine infectious anemia virus (EIAV)' Journal of Virological Methods 105 (2002) 171-179.* pCMS-EGFP Vector Information, BD Biosciences ClonetechPT3268-5, Catalog #6101-1, CloneTech PR29974; published Oct. 3, 2002, avaialble online from www.bdbiosciences.com, 13 prtinted pages.*

Definition of 'correspond' from The American Heritage Dictionary, Fourth edition, availiable online from www.bartleby.com, pp. 1-2, 2002.* pGFP vector information (1999), from www.clonetech.com, pp. 1-2.*

(Continued)

*Primary Examiner*—Stephen Kapushoc
(74) *Attorney, Agent, or Firm*—Morgan, Lewis & Bockius LLP

(57) ABSTRACT

The invention relates to a multiplex real-time RT-PCR assay with a heterologous internal control system (i.e., EGFP-RNA) for the simple and fast diagnosis of classical swine fever virus (CSFV). Primers and FAM-labeled TaqMan probes, specific for CSFV were selected by analyzing the consensus sequence of the 5'-non translated region of various CSFV strains. For determining the analytical sensitivity an in vitro transcript (T7-PC3Alf) of the 5' NTR was constructed and tested. Furthermore, a primer-probe system for the detection of the internal control sequence was established, and a multiplex assay using CSF-System 1 and the IC real-time PCR could be performed as a one-tube assay without loss of sensitivity or specificity.

36 Claims, 3 Drawing Sheets

Figure 3:
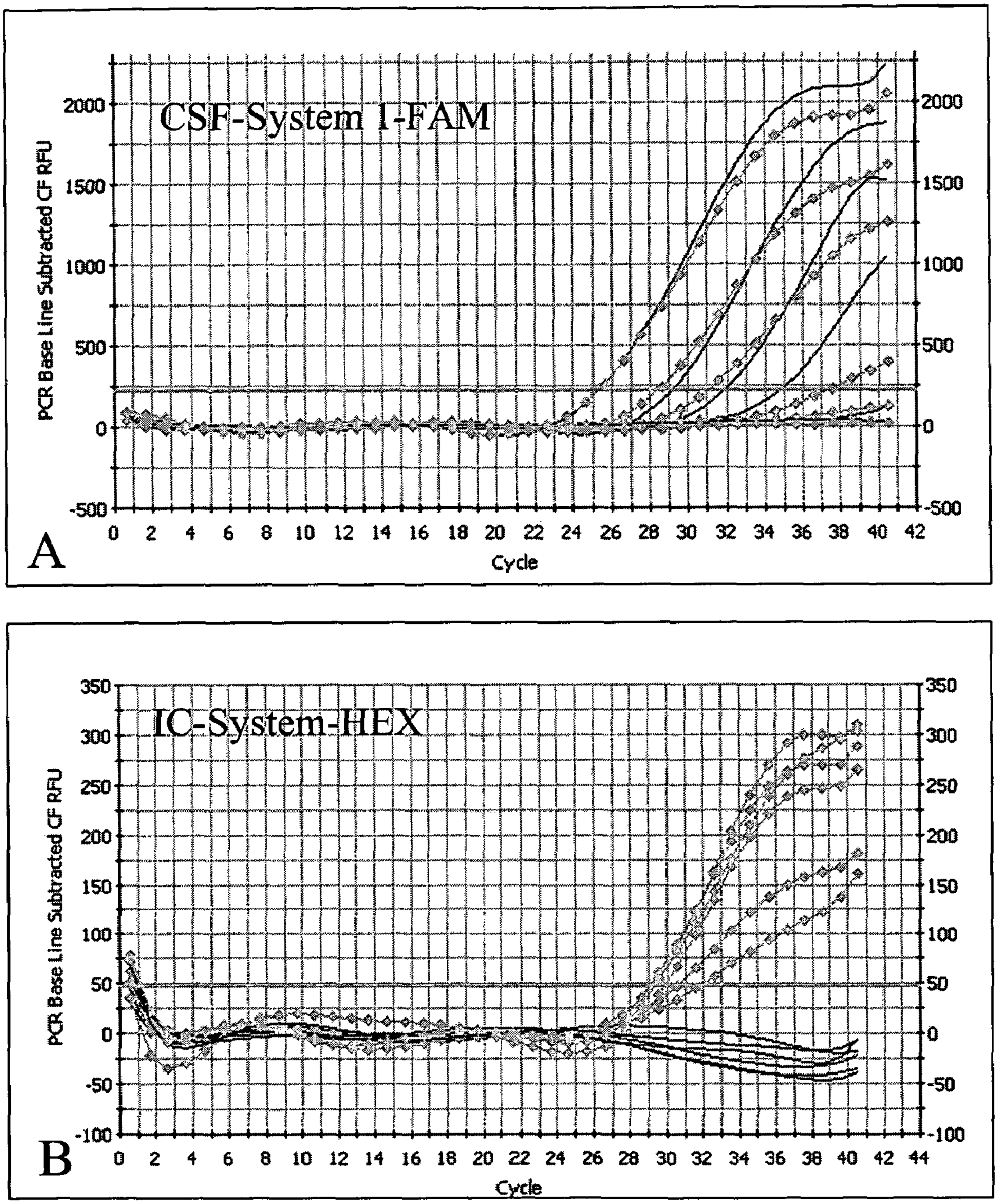

OTHER PUBLICATIONS pGFP—Sequence: 10 alignment from Blast 2 sequences results, pp. 1-4, from www.ncbi.nlm.nih.gov, 2007.*

Brown A.E. et al 'Stable and heritable gene silencing in the malaria vector *Anopheles stephensi*.' Nucleic Acids Res. Aug. 1, 2003;31(15):e85. pp. 1-6.*

Avalos-Ramirez et al., *Evidence for the presence of two novel pestivirus species*, Virology 286, (2001) 456-465.

Ausubel et al., (eds.), Current Protocols in Molecular Biology, John Wiley & Sons, N.Y. (1989), 6.3.1-6.3.6.

Barlic-Maganja and Grom, Highly Sensitive One-Tube RT-PCR and Microplate Hybridisation Assay For The Detection And For The Discrimination Of Classical Swine Fever Virus From Other *Pestiviruses, J. Virol. Methods*, 2001, 95, 101-10.

Batzer et al., *Enhanced evolutionary PCR using oligonucleotides with inosine at the 3'-terminus*, (1991) Nucleic Acid Res. 19:5081.

Belak et al., *Moleculatr diagnosis of animal diseases; some experiences over the past decade*, Rev. Mol. Diagn. (2001) 1, 434-43, Review.

Bhudevi and Weinstock, Detection of bovine viral diarrhea virus in formalin fixed paraffin embedded tissue sections by real-time RT-PCR (Taqman). *J. Virol. Methods*, 2003, 109, 25-30.

Bhudevi and Weinstock, Fluorogenic RT-PCR Assay (Taqman) For Detection And Classification Of Bovine Viral Diarrhea Virus. *Vet. Microbiol*. 2001, 83, 1-10.

Brock, T. D., *Thermus aquaticus gen.. n. and sp. n., a Non-sporulating Extreme Thermophile*, J. Bact. (1969) 98:289-297.

Cranage et al., *Identification of the human cytomegalovirus glycoprotein B gene and induction of neutralizing antibodies via its expression in recombinant vaccinia virus*, 1986, EMBO J. 5:3057-3063.

Drosten et al, 2001. Taqman 5'Nuclease Human Immunodeficiency Virus Type I PCR Assay With Phage-Packaged Competitive Internal Control for High-Throughput Blood Donor Screening. *J. Clin. Microbiol.*, 2001, 39, 4302-4308.

Edwards et al., Classical Swine Fever: The Global Situation, *Vet. Microbiol*. 2000, 73, 103-19.

Gibson et al., A Novel Method For Real Time Quantitative RT-PCR. *Genome Res*. 1996, 6, 995-1001 Heid et al., 1996.

Gorzelnik et al.,. *Validation Of Endogenous Controls For Gene Expression Studies In Human Adipocytes And Preadipocytes. Horm. Metab. Res.*, 2001, 33, 625-627.

Heid et al., *Real time quantitative PCR*, Genome Res. (1996) 6, 986-94.

Hofmann, Construction Of An Infectious Chimeric Classical Swine Fever Virus Containing The 5'UTR Of Bovine Viral Diarrhea Virus, And Its Application As A Universal Internal Positive Control In Real-Time RT-PCR. *J. Virol. Methods*, 2003, 114, 77-90.

Hyndman et al., A Novel Nested Reverse Transcription PCR Detects Bovine Viral Diarrhoea Virus In Fluids From Aborted Bovine Fetuses, *J. Virol. Methods*, 1998, 71, 69-76.

Jones et al., Quasispecies in the 5' untranslated genomic region of bovine viral diarrhea virus from a single individual, *J. Virol*. Methods, 1998, 71, 69-76.

Kiss et al., *Observations on the quasispecies composition of three animal pathogenic RNA viruses*, Acta Vet. Hung (1999) 47, 471-480.

Korimbocus et al., *Improved Detection Of Sugarcane Yellow Leaf Virus Using A Real-Time Fluorescent (Taqman) RT-PCR Assay. J. Virol. Methods*, 2002, 103, 109-120.

Kay, M.A. et al. (1997), *Gene therapy, Proc. Natl. Acad. Sci*. U.S.A. 94:12744-12746.

McGoldrick et al., *Closed one-tube reverse transcription nested polymerase chain reaction for the detection of pestiviral RNA with fluorescent probes, J. Virol*. Methods, (1999) 79, 85-95.

McGoldrick et al., A Novel Approach To The Detection Of Classical Swine Fever Virus by RT-PCR With A Fluorogenic Probe (TaqMan). *J. Virol. Methods*, 1998, 72, 125-35; 1999.

Moenning et al., Clinical Signs And Epidemiology Of Classical Swine Fever: A Review Of New Knowledge. *Vet. J.* 2003, 165, 11-20.

Ohtsuka et .al., *An Alternative Approach to Deoxyoligonucleotides as Hybridization Probes by Insertion of Deoxyinosine at Ambiguous Codon Positions**, (1985) J. Biol. Chem. 260:2605-2608.

Oshima, T et al., Isolation of an extreme thermophile and thermostability of its transfer ribonucleic acid and ribosomes, (1971)*J. Gen. Appl. Microbiol.*, 17, 513-517.

Oshima, T el al., Description of *Themus thermophilus* (Yoshida and Oshima) comb. nov. A non-sporulating thermophilic bacterium from a japanese thermall spa (1974), *Intern. System. Bacteriol*, 24, 102-112.

Degryse et al., A Comparative Analysis of Extreme Thermophilic Bacteria Belonging to the Genus Thermus., *Arch. Mircobiol*. (1978) 117: 189-196.

Paton et al., Classical Swine Fever Virus: A Ring Test To Evaluate RT-PCR Detection Methods, *Vet. Microbiol,*. 2000, 73, 159-74.

Paton, D.J., Done, S.H., Congenital Infection Of Pigs With Ruminant-Type *Pestiviruses, J. Comp. Pathol*. 1994, 111, 151-63.

Paton et al. Infection Of Pigs And Cattle With Bovine Viral Diarrhoea Virus On A Farm In England, *Vet. Rec.*, 1992, 131, 185-8.

Paton et al., Classical Swine Fever Virus: A Second Ring Test To Evaluate RT-PCR Detection Methods, *Vet. Microbiol.*, 2000, 77, 71-81.

Peters et al., Preliminary serological characterization of bovine viral diarrhea virus strains using monoclonal antibodies, *Vet. Microbiol*, (1986) 12, 195-200.

Risatti et al., Rapid Detection Of Classical Swine Fever Virus By A Portable Real-Time Reverse Transcriptase PCR Assay, *J. Clin. Microbiol*. 2003, 41, 500-5.

Rossolini et al., *Use of deoxyinosine-containing primers vs degenerate primers for polymerase chain reaction based on ambiguous sequence information*, (1994) Mol. Cell. Probes 8:91-98.

Sandvik et al., Detection And Identification Of Ruminant And Porcine *Pestiviruses* By Nested Amplification of 5' Untranslated Cdna Regions. *J. Virol. Methods*, 1997, 64, 43-56.

Schirrmeier et al., Genetic and antigenic characterization of an atypical pestivirus isolate, a putative member of a novel pestivirus species, *Journal of General Virology* (2004), 85, 3647-3652.

Terpstra, C., Wensvoort, G., A Congenital Persistent Infection Of Bovine Virus Diarrhoea Virus In Pigs: Clinical, Virological And Immunological Observations. *Vet. Q.*, 1997, 19, 97-101.

Vanderhallen et al., Classical swine fever virus is genetically stable in vitro and in vivo, *Arch. Virol*. (1999) 144, 1669-77.

Vilcek et al., *Pestiviruses* Isolated From Pigs, Cattle And Sheep Can Be Allocated Into At Least Three Genogroups Using Polymerase Chain Reaction And Restriction Endonuclease Analysis. *Arch. Virol*. 1994 136, 309-23.

Yaron et al. Intramolecularly Quenched Fluorogenic Substrates for Hydrolytic Enzymes, *Analytical Biochemistry*, 95, 228-235 (1979).

Harasawa, R., et al.: "Evidence of Pestivirus RNA in Human Virus Vaccines", J. Clin Microbiol., vol. 32(6), pp. 1604-1605, 1994.

GenBank Locus: HCVCOMGEN Hog Cholera Virus (Strain Alfort/187) Complete Genome, vol. 20, pp. 1-6, 1996.

Buck, G. A.: "Design Strategies and Performance of Custom DNA Sequencing Primers", Biotechniques, vol. 27(3), pp. 528-536, 1999.

* cited by examiner

```
1                                                                                           80
GTATACGAGG TTAGYTCRTY CTCGTRTRCA NSATYGGACA AAHYAAAATY HYDATTTGGH YYAGGGYMYC CCTCCAGCGA

81                                                                                         160
CGGCYGARCT GGGCTAGCMA TGCCCAYAGT AGGACTAGCA RACGGAGGGA MTAGCCRTAG TGGCGAGCYC CCTGGGTGKT
```

```
161                                                                                        240
CTAAGTCCTG AGTACAGGAY AGTCGTCART AGTTCRACGT RRGYDBNAGC YYRYCTYGAK ATGCTAYGTG GACGAGGGCR
```

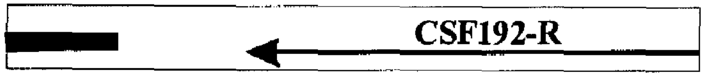

```
241                                                                                        320
YGCCCAAGAC AYAYCTTAAH YCTRGCRGGG GTHGYYAGRG YGAAATCACR YHRYGTGAKG GGRGYACGRC CTGATAGGGY

321                                                                                        400
GCYGCAGRGG CYCACTADYA RGCTAGTATA AAAAWCTCTG CTGTWCATGG CACATGGAGT TGRMTCRYTY TGAACTWTTA
```

Figure 1

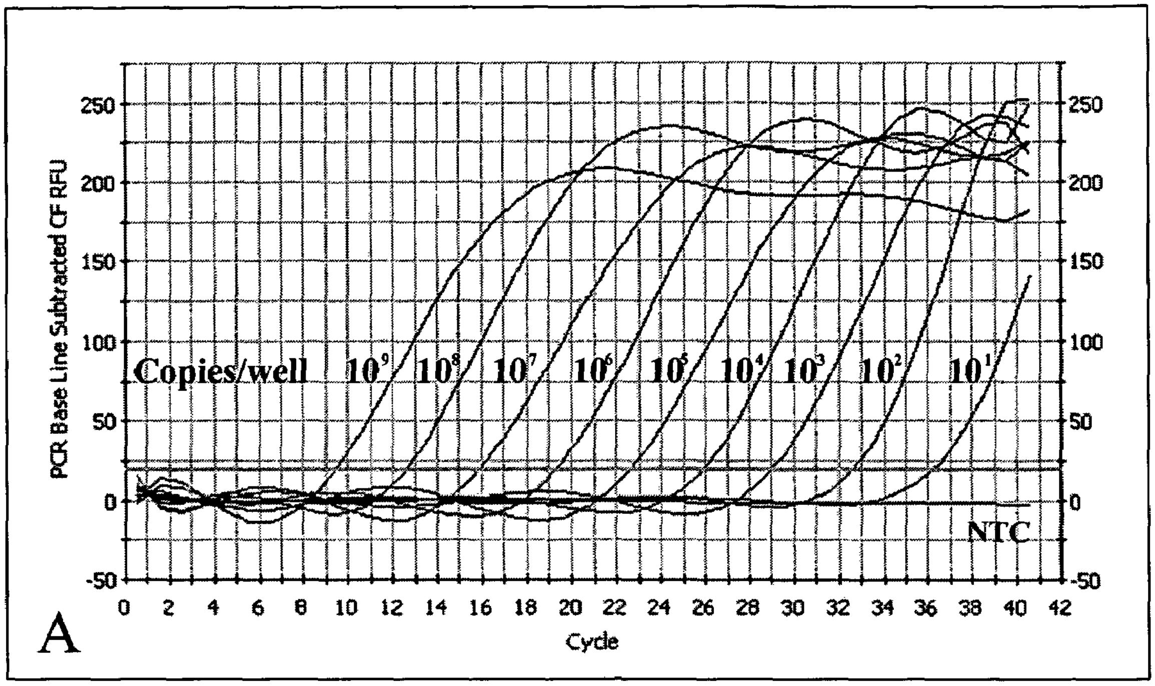
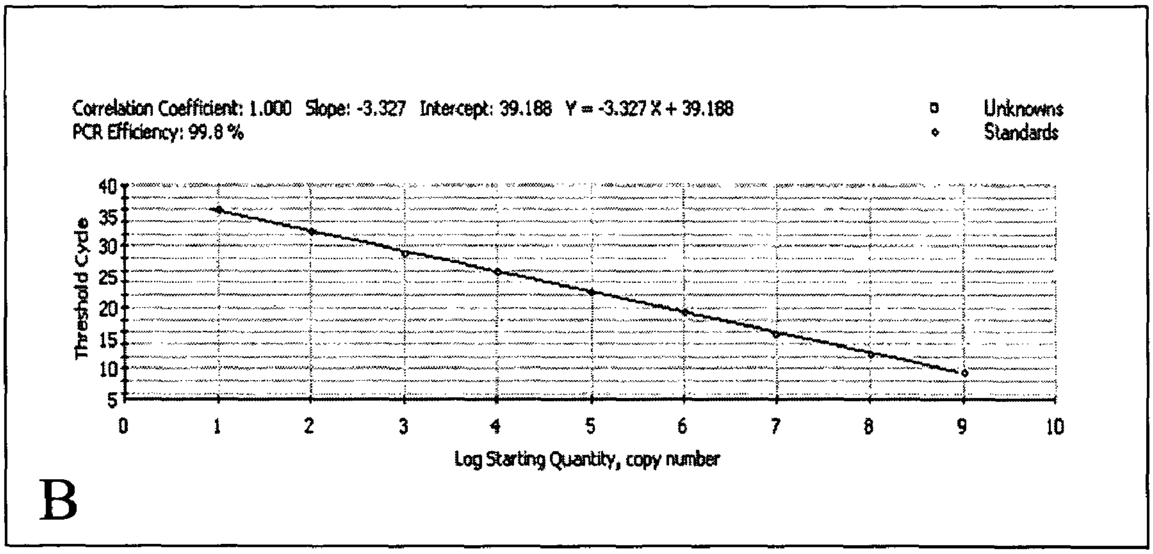
Figure 2:

SEQUENCE LISTING

<160> NUMBER OF SEQ ID NOS: 10

<210> SEQ ID NO 1
<211> LENGTH: 12298
<212> TYPE: DNA
<213> ORGANISM: Classical swine fever virus

<400> SEQUENCE: 1

```
gtatacgagg ttagttcatt ctcgtatgca tgattggaca aattaaaatt tcaatttgga     60

tcagggcctc cctccagcga cggccgaact gggctagcca tgcccacagt aggactagca    120

aacggaggga ctagccgtag tggcgagctc cctgggtggt ctaagtcctg agtacaggac    180

agtcgtcagt agttcgacgt gagcagaagc ccacctcgat atgctatgtg gacgagggca    240

tgcccaagac acaccttaac cctagcgggg gtcgctaggg tgaaatcaca ccacgtgatg    300

ggagtacgac ctgatagggt gctgcagagg cccactatta ggctagtata aaaatctctg    360

ctgtacatgg cacatggagt tgaatcattt tgaactttta tacaaaacaa acaaacaaaa    420

accaatggga gtggaggaac cggtatacga tgccacgggg aaaccattgt ttggagaccc    480

gagtgaggta cacccacaat caacactgaa gctaccacat gataggggga gaggtaacat    540

caaaacaaca ctgaagaacc tacctaggaa aggcgactgc aggagtggca accatctagg    600

cccggttagc gggatatatg taaagcccgg ccctgtcttt tatcaggact acatgggccc    660

ggtctaccat agagcccctc tagagttttt tagcgaagcg cagttttgtg aggtgaccaa    720

aaggataggt agggtgacag gtagtgacgg aaggctttac catatatatg tgtgcatcga    780

tggttgcata ctgctgaagc tagccaagag ggcgagccca agaaccctga agtggattag    840

aaatttcacc gactgtccat tgtgggttac cagttgctct gatgatggcg caagtggaag    900

taaagagaag aagccagata ggatcaacaa gggtaaatta aaaatagccc caaaagagca    960

tgagaaggac agcagaacta agccacctga cgctacgatc gtagtggaag gagtaaaata   1020

ccaggtcaaa aagaaaggta aagttaaagg aaagaatacc caagacggcc tgtaccacaa   1080

taagaataaa ccaccagaat ctaggaagaa attagaaaaa gccctattgg catgggcggt   1140

aatagcaatt atgttgtacc aaccagttga agccgaaaat ataactcaat ggaacctgag   1200

tgacaacggc actaatggta tccagcatgc tatgtacctt agagggatta gcagaagctt   1260

gcatgggatc tggccggaaa aaatatgcaa aggagtcccc acctacctgg ccacagacac   1320

ggaactgaaa gaaatacagg gaatgatgga tgccagcgag ggacaaact atacgtgctg   1380

taagttacag agacatgaat ggaacaaaca tggatggtgt aactggtaca atatagaccc   1440

ctggatacag ttgatgaata gaacccaagc aaacttggca gaaggccctc cggccaagga   1500

gtgcgctgtg acttgtaggt atgataaaga tgctgacgtc aacgtggtca cccaggccag   1560

aaacaggcca acaaccctga ccggctgcaa gaaaggaaaa aatttttctt ttgcaggtac   1620

agttatagag ggcccatgta atttcaatgt ttccgtggag gatatcttgt atggggatca   1680

tgagtgcggc agtttgctcc aggacacggc tctgtaccta gtagatggaa tgaccaacac   1740

tatagagaat gccagacagg gagcagcgag ggtaacatct tggctcggga ggcaactcag   1800

aattgccggg aagaggttgg agggtagaag caaaacctgg tttggtgcct atgccctatc   1860

accttactgt aatgtaacaa gcaaaatagg gtacatatgg tacactaaca actgcacccc   1920

ggcttgcctc cccaagaata caaagataat aggccccggt aaatttgaca ctaatgcgga   1980

ggacggaaag attctccatg agatgggcgg ccacctatca gaatttctgc tgctctctct   2040
```

-continued

```
ggttgttctg tctgacttcg cccctgaaac agccagcgcg ttatacctca ttttgcacta   2100

cgtgattcct caatcccatg aagaacctga aggctgtgac acaaaccagc tgaatctaac   2160

agtggaactc aggactgaag acgtaatacc gtcatcagtc tggaatgttg gcaaatatgt   2220

gtgtgttaga ccagactggt ggccatatga aaccaaggtg gctctgttat ttgaagaggc   2280

aggacaggtc gtaaagttag ccttacgggc gctgagggat ttaaccaggg tctggaatag   2340

cgcatcaacc acggcattcc tcatctgctt gataaaagta ttaagaggac agatcgtgca   2400

aggtgtgata tggctgctac tagtaactgg ggcacaaggc cagctagcct gcaaggaaga   2460

ttacaggtac gcaatatcat caaccaatga gatagggcta ctcggggccg gaggtctcac   2520

caccacctgg aaagaataca accacgattt gcaactgaat gacgggaccg ttaaggccat   2580

ttgcgtggca ggttccttta aagtcacagc acttaatgtg gtcagtagga ggtatttggc   2640

atcattgcat aaggaggctt tacccacttc cgtgacattc gagctcctgt tcgacgggac   2700

caacccatca actgaggaaa tgggagatga cttcgggttc gggctgtgcc cgtttgatac   2760

gagtcctgtt gtcaagggaa agtacaatac aaccttgttg aacggtagtg ctttctatct   2820

tgtctgtcca atagggtgga cgggtgttat agagtgcaca gcagtgagcc caacaactct   2880

gagaacagaa gtggtaaaga ccttcaggag ggacaagccc tttccgcaca gaatggattg   2940

tgtgaccaca acagtggaaa atgaagattt attctactgt aagttggggg gcaactggac   3000

atgtgtgaaa ggtgaaccag tggtctacac gggggggcta gtaaaacaat gcagatggtg   3060

tggctttgac ttcaatgagc ctgacggact cccacactac cccataggta agtgcatttt   3120

ggcaaatgag acaggttaca gaatagtgga ttcaacagac tgtaacagag acggtgttgt   3180

aatcagcaca gaggggagtc atgagtgctt gatcggtaac acaactgtca aggtgcatgc   3240

atcagatgaa agactgggcc ccatgccatg cagacctaaa gagatcgtct ctagtgcagg   3300

acctgtaagg aaaacttcct gtacattcaa ctacgcaaaa actttgaaga acaagtacta   3360

tgagcccagg gacagctact tccagcaata tatgcttaag ggcgagtatc agtactggtt   3420

tgacctggac gtgactgacc gccactcaga ttacttcgca gaatttgttg tcttggtggt   3480

ggtagcactg ttaggaggaa gatatatcct gtggctaata gtgacctaca tagttttaac   3540

agaacaactc gccgctggtt taccattggg ccagggtgag gtagtgttga tagggaactt   3600

aattacccac acagacattg aggtcgtagt atatttctta ctactctatt tggtcatgag   3660

ggatgagcct ataaagaaat ggatactgct gctattccat gctatgacta acaatccagt   3720

caagactata acagtggcat tgctcatggt tagcggggtt gccaggggtg gaaagataga   3780

tggcggttgg cagcggctgc cggagaccag ctttgacatc caactcgcgc tgacagttat   3840

agtagtcgct gtgatgttgc tagcaaagag agatccgact actgtcccct tggttgtaac   3900

ggtggcaacc ctgagaacgg ctaagatgac taatggactt agtacggata tagccatagc   3960

tacagtgtca acagcgttgc taacctggac ctacattagt gactattata gatacaagac   4020

ttggctacag taccttatta gcacagtgac aggtatcttt ttaataaggg tactgaaggg   4080

aataggtgag ttggatttac acactccaac cttgccatct tatagacccc tcttcttcat   4140

tctcgtgtac ctcatttcca ctgcagtggt aacaagatgg aatctggaca tagccggatt   4200

gctgttgcag tgtgtcccaa ccctttttgat ggtttttacg atgtgggcag atattctcac   4260

cttgatcctc atactgccca cttacgagtt aacaaagcta tattacctca aggaagtgaa   4320

gattggggca gaaaggggct ggttatggaa gaccaacttc aagagggtaa acgacatata   4380
```

-continued

```
cgaggttgac caagctggtg aaggggtata ccttttcccg tcaaaacaaa aaacaagttc   4440

aataacaggt accatgttgc cattgatcaa agccatactc atcagctgca tcagtaataa   4500

gtggcagttc atatacctat tgtacttgat atttgaagtg tcttactacc tccacaagaa   4560

gatcatagat gaaatagcag gagggaccaa cttcatctca agacttgtag ccgctttgat   4620

cgaagccaat tgggcctttg acaacgaaga agttagaggt ttaaagaagt tcttcctgtt   4680

gtctagtagg gttaaagaac tgatcatcaa acacaaagtg aggaatgaag taatggtcca   4740

ctggtttggt gacgaagagg tttatgggat gccgaagttg gttggcttag tcaaggcagc   4800

aacattgagt aaaaataaac attgtatttt gtgcaccgtc tgtgaagaca gagagtggag   4860

aggagaaacc tgcccaaaat gcgggcgttt tgggccacca atgacctgtg gcatgaccct   4920

agccgacttt gaagaaaaac actataagag gatctttttt agagaggatc aatcagaagg   4980

gccggttaga gaggagtacg cagggtatct gcaatacaga gccagagggc aattattcct   5040

gaggaatctc ccagtgctag caacaaaagt caagatgctc ctggtcggaa atcttgggac   5100

ggaggtggga gatttggaac accttggctg ggttcttaga gggcctgccg tttgcaagaa   5160

ggttaccgaa catgagaaat gcaccacatc cataatggat aaattgactg ctttttttcgg   5220

tgttatgcca aggggcacca cacctagagc ccctgtgaga ttccccacct ctctcttaaa   5280

gataagaagg gggttagaaa ctggctgggc gtacacacac caaggtggca ttagttcagt   5340

ggaccatgtc acttgcggga aagacttact ggtatgtgac actatgggcc ggacaagggt   5400

cgtttgccaa tcaaataata agatgacaga cgagtccgag tatggagtta aaactgactc   5460

cggatgcccg gaaggagcta ggtgttatgt gttcaaccca gaggcagtta acatatcagg   5520

gactaaagga gccatggtcc acttacaaaa gactggagga gaattcacct gtgtgacagc   5580

atcaggaact ccggccttct ttgatctcaa gaacctcaaa ggctggtcag ggctaccgat   5640

atttgaggca tcaagtggaa gggtagtcgg cagggtcaag gtcgggaaga atgaggactc   5700

taaaccaacc aagcttatga gtggaataca aacagtctcc aaaagtacca cagacttgac   5760

agaaatggta aagaaaataa cgaccatgaa caggggagaa ttcagacaaa taacccttgc   5820

tacaggtgcc ggaaaaacca cggaacttcc taggtcggtc atagaagaga tagggaggca   5880

taagagagtc ttggtcttga tccctctgag ggcggcagca gagtcagtat accagtatat   5940

gagacaaaaa catccaagca tcgcatttaa cctgaggata ggggagatga aggaagggga   6000

catggccaca gggataacct atgcctcata cggttacttc tgtcagatgc cacaacctaa   6060

gttgcgagcc gcaatggttg agtactcctt catatttctt gatgagtacc actgcgccac   6120

cccagaacaa ttggctatca tgggaaagat ccacagattt tcagagaacc tgcgggtagt   6180

agccatgacc gcaacaccag caggcacggt aacaaccaca gggcagaaac accctataga   6240

agaattcata gccccagaag tgatgaaagg ggaagactta ggctcagagt acttggacat   6300

tgctggacta aagatacctg tagaggagat gaagagcaac atgctggttt ttgtgcccac   6360

taggaacatg gcggtggaga cagcaaagaa attgaaagct aagggctaca actcaggcta   6420

ctattatagt ggagaggatc catctaacct gagagtggta acgtcacagt ccccatacgt   6480

ggtggtggca accaacgcga tagaatcagg tgttactctc ccggacttgg atgtggtcgt   6540

cgatacaggg cttaagtgtg aaaagagaat acggctgtca cctaagatgc ccttcatagt   6600

gacgggcctg aagaggatgg ctgtcacgat tggggaacaa gcccagagaa gggggagagt   6660

tgggagagta aagcctggga gatactacag gagtcaagaa actcccgttg gttctaaaga   6720

ttaccattat gatctactgc aagcacagag gtacggtatt gaagatggga taaacatcac   6780
```

-continued

```
caaatccttt agagagatga actatgattg gagcctttat gaggaggaca gtctgatgat   6840
tacacaattg gaaatcctca ataatttgtt gatatcagaa gaactaccga tggcagtaaa   6900
aaatataatg gccaggactg accacccaga accaattcag ctggcgtaca acagctacga   6960
aacacaagtg ccagtgctat tcccaaaaat aaaaaatgga gaggtgactg acagttacga   7020
taactatacc ttcctcaacg caagaaaatt gggggatgat gtaccccctt acgtgtatgc   7080
cacagaggat gaggacttag cggtagagct gctgggctta gactggccag accctgggaa   7140
ccaaggaacc gtagaggctg gcagagcact aaaacaagta gttggtctat caacagctga   7200
gaatgccctg ttagtagcct tattcggcta tgtaggatat caggcacttt caaagaggca   7260
tataccagta gtcacagata tatattcaat tgaagatcac aggttggaag acaccacaca   7320
cctacagtac gccccgaatg ctatcaagac ggaggggaag gagacagagt tgaaagagct   7380
agctcagggg gatgtgcaga gatgtgtgga agctatgacc aattatgcaa gagagggcat   7440
ccagttcatg aagtctcagg cactgaaggt gaaagaaacc cccacttaca aagagacaat   7500
ggacactgtg acggactatg taaagaaatt catggaggcg ctgacagaca gtaaagaaga   7560
catcataaaa tatgggttgt gggggacgca cacagcctta tataagagca tctgtgccag   7620
gctcgggagt gagactgcgt tcgctaccct ggtcgtgaag tggctggcat ttggggggga   7680
atcaatagca gaccatgtca aacaagcggc cacagacttg gtcgtttact atatcatcaa   7740
cagacctcag ttcccaggag acacggagac acaacaggaa ggaaggaaat ttgtggccag   7800
cctactggtc tcagctctag ttacttacac atacaaaagc tggaattaca ataatctgtc   7860
caagatagtt gaaccggctt tagccactct gccctatgcc gccacagctc tcaaactatt   7920
cgctcccact cgattggaga gcgttgtcat attgagtacc gcaatctaca aaacctacct   7980
gtcaatcagg cgcggaaaaa gcgatggttt gctaggcaca ggggttagtg cggctatgga   8040
gatcatgtca caaaatccag tatccgtggg catagcagtc atgctagggg taggggccgt   8100
ggcagcccac aatgcaatcg aagccagtga gcagaagaga acactactca tgaaagtttt   8160
tgtaaagaac ttcttggacc aggcagccac tgatgaatta gtcaaggaga gtcctgagaa   8220
aataataatg gctttgtttg aagcagtgca gacagtcggc aaccctctta gactagtata   8280
ccacctttat ggagtttttt ataaggggtg ggaggcgaaa gagttggccc aaaggacagc   8340
cggtaggaac cttttcactt tgataatgtt cgaggctgtg gaactactag gggtagatag   8400
tgaaggaaag atccgccagc tatcaagtaa ttacattcta gagctcctgt ataagttccg   8460
tgacagtatc aagtctagcg tgagggagat ggcaatcagc tgggcccctg ccccttttcag   8520
ttgtgattgg acaccgacgg atgacagaat agggctcccc caagacaatt tcctccaagt   8580
ggagacgaaa tgcccctgtg gttacaagat gaaggcagtt aagaattgtg ctggagagct   8640
aagactctta gaggaggaag gctcatttct ctgcagaaat aaattcggga gaggttcacg   8700
gaactacagg gtgacaaaat actatgatga caatctatca gaaataaagc cagtgataag   8760
aatggaaggg catgtggaac tatactacaa gggggccacc atcaaactgg atttcaacaa   8820
cagtaaaaca atattggcaa ccgataaatg ggaggttgat cactccactc tggtcagggt   8880
gctcaagagg cacacagggg ctggatatca tggggcatac ctgggcgaga aaccgaacca   8940
caaacatctg atagagaggg actgtgcaac catcaccaaa gataaggttt gttttctcaa   9000
aatgaagaga gggtgtgcat tcacttatga cttatccctt cacaacctta cccgactgat   9060
tgaattggta cacaagaata acttggaaga caaagagatc cctgctgtta cggttacgac   9120
```

-continued

```
ctggctggct tacacgtttg taaatgaaga tatagggacc ataaaaccag ccttcgggga   9180
gaaagtaaca ccggagatgc aggaggagat aaccttgcag cctgctgtag tggtggatac   9240
aactgacgtg accgtgactg tggtagggga agcccctact atgactacag gggagactcc   9300
gacagcgttc accagctcag gttcagaccc gaaaggccaa caagttttaa aactgggggt   9360
aggtgaagga caataccccg ggactaatcc acagagggca agcctgcacg aagccataca   9420
aggtgctgat gagaggccct cggtgctgat attggggtct gataaagcca cctctaatag   9480
agtaaaaact gcaaagaatg taaaggtata cagaggcagg gacccactag aagtgagaga   9540
tatgatgagg aggggaaaga tcctggtcat agccctgtct agggttgata atgctctatt   9600
gaaatttgtt gattacaaag gcacctttct aactagagag accctagagg cattaagttt   9660
gggtaggcct aaaaagaaaa acataaccaa ggcagaagca cagtggttgc tgtgccttga   9720
agaccaaatg gaagagctac ccgattggtt cgcagccggg gaacccattt ttctagaggc   9780
caacattaaa catgacaggt atcatctggt gggggatata gctactatca aggaaaaagc   9840
caaacagttg gggggctacag actccacaaa gatatctaag gaggttggtg caaaagtgta   9900
ttctatgaaa ctgagtaatt gggtgatgca agaagaaaat aaacagggca acctgacccc   9960
cttgttcgaa gagctcctgc aacagtgtcc acccgggggc cagaacaaaa ctgcacatat  10020
ggtctctgct taccaactag cccaagggaa ctggatgcca accagctgcc atgtttttat  10080
ggggaccata tctgccagga ggaccaagac ccatccatat gaagcatatg tcaagttaag  10140
ggagttggta gaggaacaca agatgaaaac attgtgtccc ggatcaagcc tgggtaagca  10200
caacgaatgg ataattggta agatcaaata ccagggaaac ctgaggacca aacacatgtt  10260
gaaccccggc aaggtggcag agcaactgtg cagagaggga cacagacgca atgtgtataa  10320
caagacaata ggctcagtaa tgacagctac tggtatcagg ttggagaaat tgcccgtggt  10380
tagggcccag acagacacaa ccaacttcca ccaagcaatc agggataaga tagacaagga  10440
agagaaccta cagaccccgg gtttacataa gaaactaatg gaggttttca atgcattgaa  10500
acgacccgag ttagagtcct cctacgatgc cgtggaatgg gaggaactgg agagaggaat  10560
aaacaggaag ggtgctgctg gtttcttcga acgcaaaaat ataggggaaa tattggattc  10620
agagaaaaac aaagtcgaag agattattga caatctgaaa aaaggtagaa acatcaaata  10680
ctatgaaact gcgatcccaa agaatgagaa gagggacgtc aatgatgact ggacctctgg  10740
tgacttcgtg gacgagaaga agcccagagt catacaatac cctgaagcaa aaacaaggct  10800
ggccatcacc aaggtgatgt ataagtgggt gaagcagaag ccagtagtta tacccgggta  10860
tgaagggaag acacctctgt tccaaatttt tgacaaagta aagaaggaat gggatcaatt  10920
ccaaaatcca gtggcagtga gcttcgacac taaggcgtgg gacacccagg taaccacaaa  10980
agatttggag ctgataaagg acatacaaaa gtactatttc aagaagaaat ggcataaatt  11040
tattgacacc ctgaccatgc atatgtcaga agtacccgta atcagcgccg atggggaagt  11100
atacataagg aaagggcaaa gaggcagtgg acaacctgac acaagcgcag gcaatagcat  11160
gctaaatgtg ttaacaatgg tttacgcctt ctgcgaggcc acgggagtac cctacaagag  11220
ctttgacagg gtggcaaaaa ttcatgtgtg cggggatgat ggtttcctga tcacagaaag  11280
ggctctcggt gagaaattcg cgagcaaggg agtccagatc ctatatgaag ctgggaagcc  11340
ccagaagatc actgaagggg ataaaatgaa agtggcctac caatttgatg atattgagtt  11400
ttgctcccat acaccaatac aagtaaggtg gtcagataac acctctagtt acatgccggg  11460
gagaaataca accacaatcc tggctaaaat ggccacaagg ttagattcca gtggtgagag  11520
```

-continued

```
gggcaccata gcatatgaga aagcagtagc attcagcttc ctgctgatgt actcctggaa  11580

cccactaatt agaaggatct gcttactggt gctatcaact gaactgcaag tgaaaccagg  11640

gaagtcaact acttactact atgaagggga cccgatatct gcctacaagg aagtcatcgg  11700

ccacaatctt tttgatctca agagaacaag cttcgagaag ctggccaaat taaatctcag  11760

catgtctgta ctcggggctt ggacaagaca caccagcaaa agactattac aagactgtgt  11820

caacatgggt gttaaagagg gcaactggct agttaatgca gacagactag tgagtagcaa  11880

gactggaaac aggtacatac ctggagaggg ccacaccctg caagggagac attatgaaga  11940

actggtgttg gcaagaaaac agatcaataa ctttcaaggg acagacaggt acaatctagg  12000

cccaatagtc aacatggtgt taaggaggct gagagtcatg atgatgaccc tgatagggag  12060

aggggtatga acgcgggcaa cccgggatct ggacccgcca gtaggaccct attgtagata  12120

acactaattt tttatttatt tagatattat tatttattta tttatttatt tattgaatga  12180

gtaagaactg gtacaaacta cctcaagtta ccacactaca ctcattttta acagcacttt  12240

agctggaagg aaaattcctg acgtccacag ttggactaag gtaatttcct aacggccc    12298


<210> SEQ ID NO 2
<211> LENGTH: 21
<212> TYPE: DNA
<213> ORGANISM: Classical swine fever virus

<400> SEQUENCE: 2

atgcccayag taggactagc a                                               21


<210> SEQ ID NO 3
<211> LENGTH: 26
<212> TYPE: DNA
<213> ORGANISM: Classical swine fever virus

<400> SEQUENCE: 3

tggcgagctc cctgggtggt ctaagt                                          26


<210> SEQ ID NO 4
<211> LENGTH: 21
<212> TYPE: DNA
<213> ORGANISM: Classical swine fever virus

<400> SEQUENCE: 4

ctactgacga ctgtcctgta c                                               21


<210> SEQ ID NO 5
<211> LENGTH: 20
<212> TYPE: DNA
<213> ORGANISM: Unknown
<220> FEATURE:
<223> OTHER INFORMATION: Enhanced Green Fluoresenct Protein probe

<400> SEQUENCE: 5

gaccactacc agcagaacac                                                 20


<210> SEQ ID NO 6
<211> LENGTH: 21
<212> TYPE: DNA
<213> ORGANISM: Unknown
<220> FEATURE:
<223> OTHER INFORMATION: Enhanced Green Fluoresenct Protein probe

<400> SEQUENCE: 6
```

-continued agcacccagt ccgccctgag c 21

<210> SEQ ID NO 7
<211> LENGTH: 16
<212> TYPE: DNA
<213> ORGANISM: Unknown
<220> FEATURE:
<223> OTHER INFORMATION: Enhanced Green Fluoresenct Protein probe

<400> SEQUENCE: 7
gaactccagg accatg 16

<210> SEQ ID NO 8
<211> LENGTH: 26
<212> TYPE: DNA
<213> ORGANISM: Classical swine fever virus
<220> FEATURE:
<221> NAME/KEY: misc_feature
<222> LOCATION: (1)..(26)
<223> OTHER INFORMATION: 5' FAM labelled
<220> FEATURE:
<221> NAME/KEY: misc_feature
<222> LOCATION: (1)..(26)
<223> OTHER INFORMATION: 3' TAMRA labelled

<400> SEQUENCE: 8
tggcgagctc cctgggtggt ctaagt 26

<210> SEQ ID NO 9
<211> LENGTH: 22
<212> TYPE: DNA
<213> ORGANISM: Unknown
<220> FEATURE:
<223> OTHER INFORMATION: Enhanced Green Fluoresenct Protein probe
<220> FEATURE:
<221> NAME/KEY: misc_feature
<222> LOCATION: (1)..(22)
<223> OTHER INFORMATION: 5' HEX labelled
<220> FEATURE:
<221> NAME/KEY: misc_feature
<222> LOCATION: (1)..(22)
<223> OTHER INFORMATION: 3' BHQ1 labelled

<400> SEQUENCE: 9
agcacccagt ccgccctgag ca 22

<210> SEQ ID NO 10
<211> LENGTH: 4151
<212> TYPE: DNA
<213> ORGANISM: Artificial Sequence
<220> FEATURE:
<223> OTHER INFORMATION: Cloning vector pEGFP-1

<400> SEQUENCE: 10
tagttattac tagcgctacc ggactcagat ctcgagctca agcttcgaat tctgcagtcg 60
acggtaccgc gggcccggga tccaccggtc gccaccatgg tgagcaaggg cgaggagctg 120
ttcaccgggg tggtgcccat cctggtcgag ctggacggcg acgtaaacgg ccacaagttc 180
agcgtgtccg gcgagggcga gggcgatgcc acctacggca agctgaccct gaagttcatc 240
tgcaccaccg gcaagctgcc cgtgccctgg cccaccctcg tgaccaccct gacctacggc 300
gtgcagtgct tcagccgcta ccccgaccac atgaagcagc acgacttctt caagtccgcc 360
atgcccgaag gctacgtcca ggagcgcacc atcttcttca aggacgacgg caactacaag 420
acccgcgccg aggtgaagtt cgagggcgac accctggtga accgcatcga gctgaagggc 480
atcgacttca aggaggacgg caacatcctg gggcacaagc tggagtacaa ctacaacagc 540

-continued

```
cacaacgtct atatcatggc cgacaagcag aagaacggca tcaaggtgaa cttcaagatc    600
cgccacaaca tcgaggacgg cagcgtgcag ctcgccgacc actaccagca gaacaccccc    660
atcggcgacg gccccgtgct gctgcccgac aaccactacc tgagcaccca gtccgccctg    720
agcaaagacc ccaacgagaa gcgcgatcac atggtcctgc tggagttcgt gaccgccgcc    780
gggatcactc tcggcatgga cgagctgtac aagtaaagcg gccgcgactc tagatcataa    840
tcagccatac cacatttgta gaggttttac ttgctttaaa aaacctccca cacctccccc    900
tgaacctgaa acataaaatg aatgcaattg ttgttgttaa cttgtttatt gcagcttata    960
atggttacaa ataaagcaat agcatcacaa atttcacaaa taaagcattt ttttcactgc   1020
attctagttg tggtttgtcc aaactcatca atgtatctta aggcgtaaat tgtaagcgtt   1080
aatattttgt taaaattcgc gttaaatttt tgttaaatca gctcattttt taaccaatag   1140
gccgaaatcg gcaaaatccc ttataaatca aaagaataga ccgagatagg gttgagtgtt   1200
gttccagttt ggaacaagag tccactatta aagaacgtgg actccaacgt caaagggcga   1260
aaaaccgtct atcagggcga tggcccacta cgtgaaccat caccctaatc aagttttttg   1320
gggtcgaggt gccgtaaagc actaaatcgg aaccctaaag ggagcccccg atttagagct   1380
tgacggggaa agccggcgaa cgtggcgaga aaggaaggga agaaagcgaa aggagcgggc   1440
gctagggcgc tggcaagtgt agcggtcacg ctgcgcgtaa ccaccacacc cgccgcgctt   1500
aatgcgccgc tacagggcgc gtcaggtggc acttttcggg gaaatgtgcg cggaacccct   1560
atttgtttat ttttctaaat acattcaaat atgtatccgc tcatgagaca ataaccctga   1620
taaatgcttc aataatattg aaaaaggaag agtcctgagg cggaaagaac cagctgtgga   1680
atgtgtgtca gttagggtgt ggaaagtccc caggctcccc agcaggcaga agtatgcaaa   1740
gcatgcatct caattagtca gcaaccaggt gtggaaagtc cccaggctcc ccagcaggca   1800
gaagtatgca aagcatgcat ctcaattagt cagcaaccat agtcccgccc ctaactccgc   1860
ccatcccgcc cctaactccg cccagttccg cccattctcc gccccatggc tgactaattt   1920
tttttattta tgcagaggcc gaggccgcct cggcctctga gctattccag aagtagtgag   1980
gaggcttttt tggaggccta ggcttttgca aagatcgatc aagagacagg atgaggatcg   2040
tttcgcatga ttgaacaaga tggattgcac gcaggttctc cggccgcttg ggtggagagg   2100
ctattcggct atgactgggc acaacagaca atcggctgct ctgatgccgc cgtgttccgg   2160
ctgtcagcgc aggggcgccc ggttcttttt gtcaagaccg acctgtccgg tgccctgaat   2220
gaactgcaag acgaggcagc gcggctatcg tggctggcca cgacgggcgt tccttgcgca   2280
gctgtgctcg acgttgtcac tgaagcggga agggactggc tgctattggg cgaagtgccg   2340
gggcaggatc tcctgtcatc tcaccttgct cctgccgaga aagtatccat catggctgat   2400
gcaatgcggc ggctgcatac gcttgatccg gctacctgcc cattcgacca ccaagcgaaa   2460
catcgcatcg agcgagcacg tactcggatg gaagccggtc ttgtcgatca ggatgatctg   2520
gacgaagagc atcaggggct cgcgccagcc gaactgttcg ccaggctcaa ggcgagcatg   2580
cccgacggcg aggatctcgt cgtgacccat ggcgatgcct gcttgccgaa tatcatggtg   2640
gaaaatggcc gcttttctgg attcatcgac tgtggccggc tgggtgtggc ggaccgctat   2700
caggacatag cgttggctac ccgtgatatt gctgaagagc ttggcggcga atgggctgac   2760
cgcttcctcg tgctttacgg tatcgccgct cccgattcgc agcgcatcgc cttctatcgc   2820
cttcttgacg agttcttctg agcgggactc tggggttcga aatgaccgac caagcgacgc   2880
```

-continued

```
ccaacctgcc atcacgagat ttcgattcca ccgccgcctt ctatgaaagg ttgggcttcg   2940

gaatcgtttt ccgggacgcc ggctggatga tcctccagcg cggggatctc atgctggagt   3000

tcttcgccca ccctaggggg aggctaactg aaacacggaa ggagacaata ccggaaggaa   3060

cccgcgctat gacggcaata aaaagacaga ataaaacgca cggtgttggg tcgtttgttc   3120

ataaacgcgg ggttcggtcc cagggctggc actctgtcga taccccaccg agaccccatt   3180

ggggccaata cgcccgcgtt tcttcctttt ccccacccca ccccccaagt tcgggtgaag   3240

gcccagggct cgcagccaac gtcggggcgg caggccctgc catagcctca ggttactcat   3300

atatacttta gattgattta aaacttcatt tttaatttaa aaggatctag gtgaagatcc   3360

tttttgataa tctcatgacc aaaatccctt aacgtgagtt ttcgttccac tgagcgtcag   3420

accccgtaga aaagatcaaa ggatcttctt gagatccttt ttttctgcgc gtaatctgct   3480

gcttgcaaac aaaaaaacca ccgctaccag cggtggtttg tttgccggat caagagctac   3540

caactctttt tccgaaggta actggcttca gcagagcgca gataccaaat actgtccttc   3600

tagtgtagcc gtagttaggc caccacttca agaactctgt agcaccgcct acatacctcg   3660

ctctgctaat cctgttacca gtggctgctg ccagtggcga taagtcgtgt cttaccgggt   3720

tggactcaag acgatagtta ccggataagg cgcagcggtc gggctgaacg gggggttcgt   3780

gcacacagcc cagcttggag cgaacgacct acaccgaact gagataccta cagcgtgagc   3840

tatgagaaag cgccacgctt cccgaaggga gaaaggcgga caggtatccg gtaagcggca   3900

gggtcggaac aggagagcgc acgagggagc ttccaggggg aaacgcctgg tatctttata   3960

gtcctgtcgg gtttcgccac ctctgacttg agcgtcgatt tttgtgatgc tcgtcagggg   4020

ggcggagcct atggaaaaac gccagcaacg cggccttttt acggttcctg gccttttgct   4080

ggccttttgc tcacatgttc tttcctgcgt tatcccctga ttctgtggat aaccgtatta   4140

ccgccatgca t                                                          4151
```

METHOD OF DETECTION OF CLASSICAL SWINE FEVER

1. CROSS-REFERENCE TO RELATED APPLICATIONS

Not Applicable.

2. STATEMENT REGARDING FEDERALLY SPONSORED RESEARCH OR DEVELOPMENT

Not Applicable.

3. INCORPORATION BY REFERENCE OF MATERIAL SUBMITTED ON A COMPACT DISC

Not Applicable.

4. FIELD OF THE INVENTION

The present invention relates to oligonucleotides useful as primers and probes. The invention also relates to methods of using the primers and probes for detection of classical swine fever virus nucleic acid, preferably in an isolated biological sample, and to reagents and kits therefor. In a particular embodiment, the invention relates to a fully validated, ready-to-use multiplex real-time reverse transcription polymerase chain reaction ("RT-PCR") assay with an internal control system for the simple and fast diagnosis of classical swine fever.

5. BACKGROUND OF THE INVENTION

Classical swine fever ("CSF") is a highly contagious disease of pigs and wild boar. Although it has been eradicated from many countries, CSF continues to cause serious problems in different parts of the world (Moenning et al., Clinical Signs And Epidemiology Of Classical Swine Fever: A Review Of New Knowledge. *Vet. J.* 2003, 165, 11-20; Edwards et al., Classical Swine Fever: The Global Situation, *Vet. Microbiol.* 2000, 73, 103-19). The causative agent, CSF virus ("CSFV") is a member of the genus *Pestivirus* within the family Flaviviridae. The other members within the genus *Pestivirus* are bovine viral diarrhoea virus ("BVDV") and border disease virus ("BDV"). The natural hosts for BVDV and BDV are cattle and sheep, respectively, but both viruses can naturally infect pigs also. Antibodies against BVD virus and BD virus may cross-react with CSFV in serological assays, and cause diagnostic problems (Terpstra, C., Wensvoort, G., A Congenital Persistent Infection Of Bovine Virus Diarrhoea Virus In Pigs: Clinical, Virological And Immunological Observations. *Vet. Q.,* 1997, 19, 97-101; Paton, D. J., Done, S. H., Congenital Infection Of Pigs With Ruminant-Type *Pestiviruses, J. Comp. Pathol.* 1994, 111,151-63; Paton et al. Infection Of Pigs And Cattle With Bovine Viral Diarrhoea Virus On A Farm In England, *Vet. Rec.,* 1992, 131, 185-8.). Because only CSFV is classified within the list A diseases of the Office International des Epizooties ("OIE"), it is important to differentiate between CSFV and BVDV or BDV.

*Pestiviruses* are small enveloped viruses containing a positive sense single stranded RNA of approximately 12.5 kb. Their genomes have a large open reading frame flanked by highly conserved 5'- and 3'-non-translated regions ("NTR"). In the last decade, mainly the 5'NTR served as the template for species and genus overlapping genome amplifications by using the RT-PCR (Vilcek et al., *Pestiviruses* Isolated From Pigs, Cattle And Sheep Can Be Allocated Into At Least Three Genogroups Using Polymerase Chain Reaction And Restriction Endonuclease Analysis. *Arch. Virol.* 1994 136, 309-23; Sandvik et al., Detection And Identification Of Ruminant And Porcine *Pestiviruses* By Nested Amplification Of 5' Untranslated Cdna Regions. *J. Virol. Methods,* 1997, 64, 43-56.; Hyndman et al., A Novel Nested Reverse Transcription PCR Detects Bovine Viral Diarrhoea Virus In Fluids From Aborted Bovine Fetuses, *J. Virol. Methods,* 1998, 71, 69-76.; Paton et al., Classical Swine Fever Virus: A Ring Test To Evaluate RT-PCR Detection Methods, *Vet. Microbiol,.* 2000, 73, 159-74; Patton et al., Classical Swine Fever Virus: A Second Ring Test To Evaluate RT-PCR Detection Methods, *Vet. Microbiol.,* 2000, 77, 71-81; Barlic-Maganja and Grom, Highly Sensitive One-Tube RT-PCR And Microplate Hybridisation Assay For The Detection And For The Discrimination Of Classical Swine Fever Virus From Other *Pestiviruses, J. Virol. Methods,* 2001, 95, 101-10). The classical RT-PCR proved to be a sensitive and specific diagnostic tool. However, detection of the amplified PCR products by gel-based systems bears the risk for cross-contaminations, does not allow exact quantification of genome copies in the template, and does not include an additional specificity test. The introduction of fluorogenic probes allows the detection of sequence specific templates achieved in real-time without opening the PCR tubes (Gibson et al., A Novel Method For Real Time Quantitative RT-PCR. *Genome Res.* 1996, 6, 995-1001 Heid et al., 1996). Since real-time PCR does not require post-PCR sample handling contaminations can be avoided, and the hybridisation of the probe ensures specificity.

For the diagnosis of *Pestiviruses*, TaqMan-probes proved to be practicable and robust and were used by several authors (McGoldrick et al., A Novel Approach To The Detection Of Classical Swine Fever Virus By RT-PCR With A Fluorogenic Probe (TaqMan). *J. Virol. Methods,* 1998, 72, 125-35; 1999; Bhudevi and Weinstock, Detection of bovine viral diarrhea virus in formalin fixed paraffin embedded tissue sections by real-time RT-PCR (Taqman). *J. Virol. Methods,* 2003, 109, 25-30; Bhudevi and Weinstock, Fluorogenic RT-PCR Assay (Taqman) For Detection And Classification Of Bovine Viral Diarrhea Virus. *Vet. Microbiol.* 2001, 83, 1-10.; Risatti et al., Rapid Detection Of Classical Swine Fever Virus By A Portable Real-Time Reverse Transcriptase PCR Assay, *J. Clin. Microbiol.* 2003, 41, 500-5). All currently described real-time RT-PCR assays for the detection of pestiviral sequences amplified targets within the 5'NTR gave results with acceptable sensitivity and specificity. However, no internal controls verifying the RNA isolation step as well as the RT-PCR have been used so far. In 2003, a multiplex real-time RT-PCR for the detection of CSFV was described in which a chimeric CSF virus containing the 5'NTR of BVDV as an universal positive control was used (Hofmann, Construction Of An Infectious Chimeric Classical Swine Fever Virus Containing The 5'UTR Of Bovine Viral Diarrhea Virus, And Its Application As A Universal Internal Positive Control In Real-Time RT-PCR. *J. Virol. Methods,* 2003, 114, 77-90). However, such a complete chimeric virion might be infectious and would therefore not be suitable for routine diagnostic purposes.

The present invention provides a robust ready to use, highly sensitive, and CSFV-specific multiplex real-time RT-PCR assay with two controls for the simple and fast routine diagnosis of CSF. The first control (positive control) proves the efficiency of primers and probes, while the second control (internal control) is designed to check RNA isolation and RT-PCR of each sample tested.

6. SUMMARY OF THE INVENTION

In one embodiment, the invention encompasses oligonucleotides that are useful as primers or probes.

In another embodiment, the invention encompasses methods for detection of classical swine fever virus nucleic acids in a biological sample using multiplex real-time RT-PCR technique with a heterologous internal control RNA (i.e., EGFP-RNA).

Another embodiment of the invention encompasses a method of quantifying CSFV viral load in an isolated, biological sample.

Yet another embodiment of the invention encompasses kits for detecting CSFV.

7. BRIEF DESCRIPTION OF THE DRAWINGS

FIG. 1: Illustrates SEQ ID NO. 11, consensus sequence of the 5'-NTR of 78' CSFV strains and the localisation of the CSFV-specific real-time RT-PCR system 1. The consensus sequence was depicted using the single letter code of nucleotides. Underlined letters characterized wobble sequences with a preference for a specific nucleotide. Only 1 to 3 of the compared 78 nucleotides were divergent. With wobble sequences printed in bold, alignments were characterised which were divergent in 4 or more nucleotides.

FIG. 2: Analytical sensitivity of CSF-System 1 based on the 10 fold dilution series of the in vitro transcribed PC. The amplification blot (A) and the associated standard curve graph (B) were depicted. (NTC=no template control)

FIG. 3: Sensitivity of the CSF-System 1 multiplex assay compared with the single assay. In FIG. 3A are depicted the FAM fluorescence values of both assays. In FIG. 3B the co-amplification of IC-RNA was demonstrated. Only for the multiplex assays HEX fluorescence values were observed. (black lines=single assay; grey lines with squares=multiplex assay).

8. DETAILED DESCRIPTION OF THE INVENTION

8.1. Definitions

As used herein the term "amplified" or "amplification" refers to the production of many DNA copies from one or a few copies.

As used herein the term "biological sample" includes, but is not limited to, to serum, plasma, semen, urine, or blood.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes, but is not limited to, ionic, non-ionic, Van der Waals, hydrophobic interactions. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

As used herein the term "conservative amino acid substitution" refers to a substitution in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, the terms "fragment of a CSFV" or "portion of a CSFV" refer to an amino acid sequence comprising at least about 5%, 10%, 20%, 30%, 40%, 50%, 60%, 70%, 80%, 90%, 95%, 96%, 97%, 98%, 99% or 100% of a naturally occurring CSFV or mutant thereof.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters. In addition, the terms "gene" and "recombinant gene" also refer to nucleic acid molecules comprising an open reading frame encoding an CSFV.

As used herein, a "heterologous polynucleotide" or a "heterologous nucleic acid" or a "heterologous gene" or a "heterologous sequence" or an "exogenous DNA segment" refers to a polynucleotide, nucleic acid or DNA segment that originates from a source foreign to the particular host cell, or, if from the same source, is modified from its original form. A heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. As an example, a signal sequence native to a yeast cell but attached to a human CSFV sequence is heterologous.

A "homologous nucleic acid sequence" or "homologous amino acid sequence," or variations thereof, refer to sequences characterized by a homology at the nucleotide level or amino acid level. Homologous nucleotide sequences encode those sequences coding for isoforms of peptides. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a CSFV of species other than humans, including, but not limited to, mammals, and thus can include, for example, mouse, rat, rabbit, dog, cat, pig, cow, horse, and other organisms. Homologous nucleotide sequences also include, but are not limited to, naturally occurring allelic variations and mutations of the nucleotide sequences set forth herein.

As used herein, an "isolated" nucleic acid sequence refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semi-synthetic, synthetic origin, or any combinations thereof.

As used herein the term "multiplex PCR" refers to PCR, which involves adding more than one set of PCR primers to the reaction in order to target multiple locations throughout the genome; it is useful for DNA typing because, inter alia, the probability of identical alleles in two individuals decreases with an increase in the number of polymorphic loci examined. Furthermore, multiplexing with an IC (e.g., EGFP-RNA) provides internal control of the whole PCR without affecting sensitivity or specificity of the CSFV real-time PCR.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

As used herein the abbreviation "nt" means nucleotide(s).

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. Oligonucleotides of the invention may be chemically synthesized and may be used as probes.

As used herein, a DNA segment is referred to as "operably linked" or "operatively linked" when it is placed into a functional relationship with another DNA segment. Generally, DNA sequences that are operably linked are contiguous, and in the case of a signal sequence or fusion protein both contiguous and in reading phase. However, enhancers need not be contiguous with the coding sequences whose transcription they control. Linking, in this context, is accomplished by ligation at convenient restriction sites or at adapters or linkers inserted in lieu thereof.

As used herein, "PCR" generally refers to a method for amplifying a DNA or RNA base sequence using a heat-stable polymerase and two oligonucleotide primers, one complementary to the (+)-strand at one end of the sequence to be amplified and the other complementary to the (−)-strand at the other end. Because the newly synthesized DNA or cDNA strands can subsequently serve as additional templates for the same primer sequences, successive rounds of primer annealing, strand elongation, and dissociation produce rapid and highly specific amplification of the desired sequence.

As used herein, the term "probes" refer to nucleic acid sequences of variable length, preferably between at least about 10 nt or about 100 nt depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies, preferably PCR, more preferably RT-PCR, and even more preferably in real-time RT-PCR.

As used herein, the term "primer" refers to a short, artificial oligonucleotide strands usually not more than fifty, preferably 18-25 bp nucleotides (since DNA is usually double-stranded, its length is measured in base pairs; the length of single-stranded DNA is measured in bases or nucleotides) that exactly match the beginning and end of the genomic fragment to be amplified. Primers anneal (adhere) to the DNA template at the starting and ending points, where the DNA-Polymerase binds and begins the synthesis of the new DNA strand. The choice of the length of the primers and their melting temperature (Tm) depends on a number of considerations. The melting temperature of a primer—not to be confused with the melting temperature of the DNA in the first step of the PCR process—is defined as the temperature below which the primer will anneal to the DNA template and above which the primer will dissociate (break apart) from the DNA template. The melting temperature increases with the length of the primer. Primers that are too short would anneal at several positions on a long DNA template, which would result in non-specific copies. On the other hand, the length of a primer is limited by the temperature required to melt it. Melting temperatures that are too high, (i.e., above 80° C.), can also cause problems since the DNA-Polymerase is less active at such temperatures. The optimum melting temperature is between 60° C. and 75° C. A forward sequencing primer anneals 5' with respect to the reverse primer, and the reverse sequencing primer that anneals 3' with respect to the forward primer. The relationship between the primers and the reference sequence depends on the coordinate system that is used. The forward primer's annealing positions will usually be less than the annealing positions of the reverse primer since the forward primer should fall to the logical left of the reverse primer in the coordinate system.

As used herein, the term "promoter" refers to a region of DNA involved in binding RNA polymerase to initiate transcription.

As used herein, the term "recombinant" refers to a cell, tissue or organism that has undergone transformation with a new combination of genes or DNA.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide. Stringent conditions are known to those skilled in the art and can be found in Ausubel et al., (eds.), Current Protocols in Molecular Biology, John Wiley & Sons, N.Y. (1989), 6.3.1-6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C.

As used herein, the term "subject" can be a human, or an animal, preferably a pig, cow, sheep, or boar.

As used herein, the term "TaqMan" generally refers to the probe used to detect specific sequences in PCR products by employing the 5'-->3' exonuclease activity of Taq DNA polymerase. The TaqMan probe (about 20-30 bp), disabled from extension at the 3' end, consists of a site-specific sequence labeled with a fluorescent reporter dye and a fluorescent quencher dye. During PCR the TaqMan probe hybridizes to its complementary single strand DNA sequence within the PCR target. When amplification occurs the TaqMan probe is degraded due to the 5'-->3' exonuclease activity of Taq DNA polymerase, thereby separating the quencher from the reporter during extension. Due to the release of the quenching effect on the reporter, the fluorescence intensity of the reporter dye increases. During the entire amplification process this light emission increases exponentially, the final level being measured by spectrophotometry after termination of the PCR. Because increase of the fluorescence intensity of the reporter dye is only achieved when probe hybridization and amplification of the target sequence has occurred, the TaqMan assay offers a sensitive method to determine the presence or absence of specific sequences. Therefore, this technique is particularly useful in diagnostic applications, such as the screening of samples for the presence or incorporation of favorable traits and the detection of pathogens and diseases. The TaqMan assay allows high sample throughput because no gel-electrophoresis is required for detection. TaqMan probes depend on the 5'-nuclease activity of the DNA polymerase used for PCR to hydrolyze an oligonucleotide that is hybridized to the target amplicon. In particular, TaqMan probes are oligonucleotides that have a fluorescent reporter dye attached to the 5' end and a quencher moeity coupled to the 3' end. These probes are designed to hybridize to an internal region of a PCR product. In the unhybridized state, the proximity of the fluorescent reporter and the quench molecules prevents the detection of fluorescent signal from the probe. During PCR, when the polymerase replicates a template on which a TaqMan probe is bound, the 5'-nuclease activity of the polymerase cleaves the probe. This decouples the fluorescent and quenching dyes and the Fluorescence Resonance Energy Transfer (FRET) no longer occurs. Thus, fluorescence increases in each cycle, proportional to the amount of probe cleavage.

As used herein, the term "thermostable polymerase enzyme" refers to an enzyme, which is stable to heat and is heat resistant and catalyzes (facilitates) combination of the nucleotides in the proper manner to form the primer extension products that are complementary to each nucleic acid strand. Generally, the synthesis will be initiated at the 3' end of primer and will proceed in the 5' direction along the template strand, until synthesis terminates, producing molecules of different lengths. There may be a thermostable enzyme, however, which initiates synthesis at the 5' end and proceeds in the other direction, using the same process as described above. The preferred thermostable enzyme herein is a DNA polymerase isolated from *Thermus aquaticus*. Various strains thereof are available from the Americal Type Culture Collection, Rockville, Md., and are described by T. D. Brock, J. Bact. (1969) 98:289-297, and by T. Oshima, *Arch. Mircobiol*. (1978) 117:189-196. One of these preferred strains is strain YT-1.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

"Variants or variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide.

As used herein, the term "vector" refers broadly to any plasmid, phagemid or virus encoding an exogenous nucleic acid. The term is also be construed to include non-plasmid, non-phagemid and non-viral compounds which facilitate the transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997*, Proc. Natl. Acad. Sci. U.S.A.* 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO 94/17810, published Aug. 18, 1994; International Patent Application No. WO 94/23744, published Oct. 27, 1994). Examples of non-viral vectors include, but are not limited to, liposomes, polyamine derivatives of DNA, and the like.

As used herein, the term "wild type" refers to a polynucleotide or polypeptide sequence that is naturally occurring.

8.2. Description of the Embodiments of the Invention

8.2.1. Oligonucleotides of the Invention

The invention encompasses oligonucleotides that are useful as primers or probes. When used as a probe, it is preferable that the oligonucleotides contain a label. In an illustrative embodiment, the oligonucleotides of the invention encompass an oligonucleotide having the nucleotide sequence of SEQ ID NO: 2, SEQ ID NO: 3, SEQ ID NO: 4, SEQ ID NO: 5, SEQ ID NO. 6, SEQ ID NO:7, SEQ ID NO. 8, or SEQ ID NO. 9. It is preferred that the oligonucleotides of the invention are useful as primers or probes. A particular embodiment of the invention encompasses a set of primers of oligonucleotides of SEQ ID NO: 2, SEQ ID NO: 4, SEQ ID NO: 5, and SEQ ID NO: 7. Another particular embodiment of the invention encompasses a set of probes of oligonucleotides of SEQ ID NO: 3, SEQ ID NO: 6, SEQ ID NO. 8, or SEQ ID NO. 9. In another embodiment, the probes of the invention further comprise a label. In a particular embodiment, the label is a fluorescent group, digoxigenin, or biotin.

Illustrative oligonucleotides of the invention have the following nucleotide sequences:

```
                                        SEQ ID NO. 2
5'-ATGCCCAYAGTAGGACTAGCA-3':

                                        SEQ ID NO. 3
5'-TGGCGAGCTCCCTGGGTGGTCTAAGT-3':

                                        SEQ ID NO. 4
5'-CTACTGACGACTGTCCTGTAC-3':

                                        SEQ ID NO. 5
5'-GACCACTACCAGCAGAACAC-3':

                                        SEQ ID NO. 6
5'-AGCACCCAGTCCGCCCTGAGCA-3':

                                        SEQ ID NO. 7
5'-GAACTCCAGGACCATG-3':

                                        SEQ ID NO. 8
5'-FAM-TGGCGAGCTCCCTGGGTGGTCTAAGT-TAMRA-3':

                                        SEQ ID NO. 9
5'-HEX-AGCACCCAGTCCGCCCTGAGCA-BHQ1-3':
```

8.2.1.1. Oligonucleotide Synthesis

Oligonucleotide synthesis has become routine. For a detailed description of nucleic acid synthesis see Gait, M. J., *Oligonucleotide Synthesis: a Practical Approach*. IRL Press, Oxford England. Preferably, the oligonucleotides of the invention are synthesized on supports in what is known as solid phase synthesis. Alternatively, they are synthesized in solution. Those of ordinary skill in the art will recognize that both labeled, unlabeled and/or modified oligonucleotides (DNA, RNA and synthetic analogues thereof) are readily available. They can be synthesized using commercially available instrumentation and reagents or they can be purchased from commercial vendors of custom manufactured oligonucleotides. Patents that discuss various compositions, supports and methodologies for the synthesis and labeling of nucleic acids include: U.S. Pat. Nos. 5,476,925, 5,453,496, 5,446,137, 5,419,966, 5,391,723, 5,391,667, 5,380,833, 5,348,868, 5,281,701, 5,278,302, 5,262,530, 5,243,038, 5,218,103, 5,204,456, 5,204,455, 5,198,527, 5,175,209, 5,164,491, 5,112,962, 5,071,974, 5,047,524, 4,980,460, 4,923,901, 4,786,724, 4,725,677, 4,659,774, 4,500,707, 4,458,066, and 4,415,732, each of which is incorporated by reference.

8.2.2. Methods of the Invention

The invention also encompasses methods for detection of CSFV nucleic acids in an isolated biological sample of a subject comprising reverse transcribing RNA encoding one or more CSFV genes to obtain complementary CSFV ("CSFV cDNA"); amplifying said CSFV cDNA utilizing two or more primers under conditions to produce a PCR Product, wherein at least one forward primer hybridizes to a target site corresponding to a first group of nucleotides of the SEQ ID NO: 1 or a complementary strand thereof and at least one reverse primer hybridizes to a target site corresponding to second group of nucleotides of SEQ ID NO: 1 or a complementary strand thereof; contacting said PCR Product with a nucleic acid probe such that the probe hybridizes to the PCR Product or a complementary strand thereof to provide a hybridized probe, and detecting the presence of the hybridized probe.

In an illustrative embodiment, the invention encompasses a method for detecting CSFV nucleic acids in a biological sample comprising:

(i) reverse transcribing said nucleic acids to obtain CSFV cDNA;

(ii) contacting said CSFV cDNA with two or more primers and a DNA polymerase to produce a PCR Product, wherein the primers comprise at least one forward primer and at least one reverse primer, under conditions such that the primers hybridize to the cDNA, wherein at least one forward primer hybridizes to a target site corresponding to nucleotides 75 to 150, preferably nucleotides 90 to 130, and most preferably nucleotides 100 to 120 of SEQ ID NO: 1 or a complementary strand thereof and at least one reverse primer hybridizes to a target site corresponding to nucleotides 155 to 205, preferably nucleotides 165 to 195, and most preferably nucleotides 172 to 192 of SEQ ID NO: 1 or a complementary strand thereof;

(iii) contacting the PCR Product with a first nucleic acid probe such that the probe hybridizes to the PCR Product at a target site corresponding to nucleotides 130 to 175, preferably nucleotides 135 to 170, and most preferably nucleotides 141 to 166 of SEQ ID NO: 1 or a complementary strand thereof to provide a hybridized probe; and (iv) detecting the presence of the hybridized probe.

In another embodiment, the invention encompasses further adding an internal control of the EGFP-Sequence of plasmid vector pEGFP-1 (i.e., SEQ ID NO. 10).

In another embodiment, the invention further comprises adding at least one second forward primer and at least one second reverse primer idize to said additional primer.

In another illustrative embodiment, a second forward primer hybridizes to a target site corresponding to nucleotides 625 and 675, preferably nucleotides 630 to 665, and most preferably nucleotides 637 to 656 of SEQ. ID NO. 10 or a complementary strand thereof, and the second reverse primer hybridizes to a target site corresponding to nucleotides 740 to 780, preferably nucleotides 745 to 775, and most preferably nucleotides 750 to 768 of SEQ ID NO. 10 or a complementary strand thereof.

Another illustrative embodiment of the invention encompasses adding a second nucleic acid probe, wherein the probe hybridizes to SEQ. ID NO. 10 or a complementary strand thereof.

In another illustrative embodiment, the second nucleic acid probe hybridizes to a target site corresponding to nucleotides 690 to 735, preferably nucleotides 695 to 730, and most preferably nucleotides 703 to 724 of SEQ ID NO. 10 or a complementary strand thereof.

Another illustrative embodiment of the invention encompasses a method for detection of CSFV nucleic acids in a biological sample comprising:

(i) reverse transcribing said nucleic acids to obtain a complementary CSFV complex (i.e., CSFV cDNA);

(ii) contacting said CSFV cDNA with two or more first primers and a DNA polymerase to produce a PCR Product, wherein a first forward primer hybridizes to a target site corresponding to nucleotides 100 to 120 of SEQ ID NO. 1 or a complementary strand thereof and a first reverse primer hybridizes to a target site corresponding to nucleotides 172 to 192 of SEQ ID NO. 1 or a complementary strand thereof;

(iii) contacting the PCR Product with a first nucleic acid probe such that the probe hybridizes to a target site corresponding to nucleotides 141 to 166 of SEQ ID 1 or a complementary strand thereof, (iv) adding an internal control and at least two or more second primers such that at least one second forward primer hybridizes to a target site corresponding to nucleotides 637 to 656 of SEQ ID NO. 10 or a complementary strand thereof and at least one second reverse primer hybridizes to a target site corresponding to nucleotides 750 to 768 of SEQ ID NO 10 or a complementary strand thereof;

(v) adding at least one second nucleic acid probe such that the probe hybridizes to a target site corresponding to nucleotides 703 to 724 of SEQ ID 10 or a complementary strand thereof;

(vi) detecting the presence of the hybridized probes.

In another particular embodiment of the methods of the invention, the probe can be independently detected in a closed tube format in either real-time or at the end-point of the assay. In yet another particular embodiment of the methods of the invention, at least two or more independently detectable PCR Products are present in a single multiplex assay that is used to simultaneously detect, identify or quantitate two or more target molecules of interest (e.g., CSFV nucleic acids) in the same sample and in the same assay.

In another embodiment the invention encompasses methods for multiplex real-time RT-PCR detection of CSFV nucleic acids in a biological sample comprising reverse transcribing RNA encoding CSFV genes to obtain a CSFV cDNA and amplifying said CSFV cDNA with at least one forward primer (i.e., a first forward primer) and at least one reverse primer (i.e., a first reverse primer) under conditions such that said primers hybridize to said cDNA to form a PCR Product, wherein at least one forward primer hybridizes to a target site corresponding to a first group of nucleotides of the SEQ ID NO. 1 and at least one reverse primer hybridizes to a target site corresponding to second group of nucleotides of SEQ ID NO. 1; contacting the PCR Product with a first nucleic acid probe wherein the probe hybridizes to the PCR Product or a complementary strand thereof to form a hybridization probe, and detecting the presence of the hybridization probe. The invention further comprises the presence of an internal control of SEQ ID NO. 10 and two or more additional forward primers (i.e., a second forward primer) and two or more additional reverse primers (i.e., a second reverse primer), wherein at least one additional forward primer hybridizes to a target site corresponding to a first group of nucleotides of the SEQ ID NO. 10 or a complementary strand thereof and at least one additional reverse primer hybridizes to a target site corresponding to second group of nucleotides of SEQ ID NO. 10 or a complementary strand thereof and further comprises addition of a second nucleic acid probe, wherein the second probe hybridizes to a target site corresponding to group of nucleotides of SEQ ID 10 or a complementary strand thereof.

In an illustrative embodiment, the first forward primer hybridizes to a target site corresponding to nucleotides 75 to 150, preferably nucleotides 90 to 130, and most preferably nucleotides 100 to 120 of SEQ ID NO. 1 or a complementary strand thereof. In another illustrative embodiment, the first reverse primer hybridizes to a target site corresponding to nucleotides 155 to 205, preferably nucleotides 165 to 195, and most preferably nucleotides 172 to 192 of SEQ ID NO. 1 or a complementary strand thereof. In another illustrative embodiment, the first probe hybridizes to a target site corresponding to nucleotides 130 to 175, preferably nucleotides 135 to 170, and most preferably nucleotides 141 to 166 of SEQ ID NO. 1 or a complementary strand thereof.

In another illustrative embodiment, the second forward primer hybridizes to a target site corresponding to nucleotides 625 to 675, preferably nucleotides 630 to 665, and most preferably nucleotides 637 to 656 of SEQ ID NO. 10 or a complementary strand thereof. In another illustrative embodiment, the second reverse primer hybridizes to a target site corresponding to nucleotides 740 to 780 preferably nucleotides 745 to 775, and most preferably nucleotides 750 to 768 of SEQ ID NO 10 or a complementary strand thereof. In another illustrative embodiment, the second probe hybridizes to a target site corresponding to nucleotides 690 to 735, preferably nucleotides 695 to 730, and most preferably nucleotides 703 to 724 of SEQ ID NO 10 or a complementary strand thereof.

In a particular embodiment, the invention encompasses a standardized, sensitive CSFV-specific multiplex real-time RT-PCR for the detection of CSFV genomes including a heterologous internal control ("IC") in a one-tube protocol. According to an embodiment of the invention, both primers (e.g., the forward and reverse primer) and a TaqMan-probe were selected using a 5'-NTR consensus sequence of 78 different CSFV strains that illustrated 100% matching oligonucleotides were chosen, and only a small group of CSFV isolates had primer binding sites with maximal one nucleotide exchange compared to the published CSFV sequences. The CSFV primers and TaqMan-probe of a CSF-System 1 enabled the detection of genome sequences with up to 2 mismatches in the probe region. The "CSF-System 1" consists of the primer pair CSF100-F/CSF192-R, and the FAM-labelled probe CSF-Probe 1 (FIG. 1, Table 1), and amplifies a fragment of 93 bp between nt 100 and 192 of the 5'-NTR of CSFV (strain Alfort 187 [Accession No. X87939]; FIG. 1). The detection of all different CSFV strains and isolates could be assumed, and all tests with a large panel of CSFV of different genotypes showed the ability of CSF-System 1 to detect all CSFV strains and isolates. In order to prove the species specifity of CSF-System 1, a large panel of different BDV, BVDV 1, BVDV 2, and atypical *Pestiviruses* was examined resulting in 100% CSF specificity.

The IC is used to avoid false negative results due to RNA degradation or inhibitory effects. (Hofmann, *Construction Of An Infectious Chimeric Classical Swine Fever Virus Containing The 5'UTR Of Bovine Viral Diarrhea Virus, And Its Application As A Universal Internal Positive Control In Real-Time RT-PCR; J. Virol. Methods,* 2003, 114, 77-90.). In vitro-transcribed EGFP RNA, which was detected using an independent primer/probe system, can be used as the internal control. This IC can be also used in multiplex PCR assays for other pathogens. Alternatively, a housekeeping gene or an internal control which mimics the targeted CSFV sequence can be used (Gorzelnik et al., *Validation Of Endogenous Controls For Gene Expression Studies In Human Adipocytes And Preadipocytes. Horm. Metab. Res.,* 2001, 33, 625-627; Korimbocus et al., *Improved Detection Of Sugarcane Yellow Leaf Virus Using A Real-Time Fluorescent (Taqman) RT-PCR Assay. J. Virol. Methods,* 2002, 103, 109-120;). However, housekeeping genes have the disadvantage that their concentrations are unknown, especially in cell-free samples like plasma or serum. In contrast to a recently published CSFV multiplex PCR (e.g., Hofmann, 2003), the use of infectious, genetically engineered CSFV is avoided, so the IC system of the present invention can also be used in standard, non biosafety level 2 laboratories. Using heterologous in vitro-transcribed RNA as IC does not completely simulate RNA extraction from packaged RNAse-protected viral RNA (Drosten et al, 2001. *Taqman 5'Nuclease Human Immunodeficiency Virus Type* 1 *PCR Assay With Phage-Packaged Competitive Internal Control For High-Throughput Blood Donor Screening. J. Clin. Microbiol.,* 2001, 39, 4302-4308). Neither IC RNA degradation nor release of RNA from virions during the extraction step was crucial for CSFV RNA extraction. Therefore, the present invention offers a universal, non-infectious IC RNA, which was demonstrated to be stable even after 40 freeze/thaw cycles.

The present invention allows the use of a marked low concentration of the IC, a strictly limited amount of IC primers, and an IC amplicon, which is selected to be significantly longer than the CSFV-specific amplicon to enable on one hand, a high sensitivity of CSF System 1 and, on the other hand, to allow a relatively constant amplification of the IC in the multiplex assay. As a consequence, identical analytical sensitivities for the single and the multplex CSF assay can be achieved. Using $\log_2$-dilutions of an in vitro-transcribed positive RNA, a mean detection limit of 8 copies per RT-PCR reaction is attained in combination with a wide dynamic range of 9 $\log_{10}$ steps for the single and the multiplex systems. Nevertheless, an inhibition of the IC amplification could be observed using very high amounts of target RNA. This partial or complete inhibition of IC amplification is tolerable, since the IC is used to exclude false negative results, which are irrelevant in the case of high amounts of CSFV target RNA (Hofmann, 2003, see supra). Furthermore, the sensitivity of the CSF-System 1 multiplex RT-PCR is comparable to that of virus isolation, which is regarded as a 'gold standard' in CSF diagnosis. Furthermore, the sensitivity of the cell culture system used as a 'gold standard' is crucial for the calculation and results can therefore be different for cell culture-adapted strains like the CSFV Alfort 187 in comparison to CSFV field isolates.

The analysis of 36 CSFV isolates of various genotypes with the multiplex version of CSF-System 1 showed similar detection characteristics for all CSFV. Even in the case of the genotype 3.4 CSFV strain "Kanagawa," no differences concerning the fluorescence signals and threshold cycles were observed. In contrast to our CSF-System 1, a published CSFV specific real-time RT-PCR assay, based on sequences located more downstream within the 5'NTR, generated only shallow fluorescence curves with the "Kanagawa" strain (McGoldrick et al., 1998).

For an efficient control of the CSFV primers and the TaqMan-probe, a plasmid-based, non-infectious positive control is constructed. Dilution series of the in vitro-transcribed positive control RNA are used as a standard to quantify the viral RNA contained in CSFV positive samples. Therefore both controls (IC and PC) in the multiplex CSF-System 1 of the invention are in-vitro-transcribed, non-infectious RNAs.

The present invention further encompasses a two-color multiplex real-time RT-PCR system encompassing: (a) "one tube" RT-PCR reaction, (b) use of a validated and highly efficient RT-PCR-kit, (c) integration of a stable and non-infectious IC, (d) use of a quantifiable, non-infectious PC, and (e) validation of the complete system as a highly sensitive and CSFV-specific two-colour multiplex RT-PCR reaction.

Particularly, the real time RT-PCR method of the present invention allows transiently-infected pigs with no clinical signs of CSFV to be detected earlier, more often, and for a longer time period than with cell culture isolation methods. The standardized PCR system can be used as a robust tool for the highly sensitive and specific detection of CSFV in eradication campaigns or in case of emergencies.

8.2.2.1. Multiplex Analysis

In a preferred embodiment of this invention, a multiplex hybridization assay is performed. Multiplex analysis relies on the ability to sort sample components or the data associated therewith, during or after the assay is completed. In preferred embodiments of the invention, distinct independently detectable moieties are used to label component of two or more different complexes. The ability to differentiate between and/or quantitate each of the independently detectable moieties provides the means to multiplex a hybridization assay because the data which correlates with the hybridization of each of the distinctly (independently) labeled complexes to a target sequence can be correlated with the presence, absence or quantity of each target sequence or target molecule sought to be detected in a sample.

Consequently, the multiplex assays of this invention may be used to simultaneously detect the presence, absence or quantity of two or more target sequence or target molecule in the same sample and in the same assay. Because the complexes are self-indicating, and can be designed to be independently detectable, the multiplex assays of this invention can be performed in a closed tube format to provide data for simultaneous real-time and end-point analysis of a sample for two or more target sequences or target molecules of interest in the same assay. Additionally, the assays can be further multiplexed by the incorporation of unimolecular probes to thereby confirm assay performance or be used to identify a specific feature of a target sequence or target molecule of interest.

8.2.2.2. Multiplex Applications

As illustrated by the examples that follow, the oligonucleotides of the invention are particularly useful for applications involving multiple oligonucleotides sets wherein each oligonucleotide contains at least one independently detectable moiety. Preferably, the independently detectable moieties are independently detectable fluorophores. For example, a mixture of one or more different oligonucleotides may be used to detect each of four different target sequences, wherein one or more oligonucleotides comprises one or more independently detectable fluorophores. For this example, detection of the presence, absence or quantity of the different target sequences is made possible by the detection and/or quantitation of each of the different independently detectable fluorophores after the mixture has been incubated with the sample of interest. As previously discussed, the oligonucleotides may also be used in assays wherein the independently detectable moieties are used to distinguish the operation of the same or different processes occurring in the same assay. Such multiplex assays are possible whether the oligonucleotides are used as probes or as primers.

8.2.3. Probes of the Invention

Another embodiment of the invention encompasses a first probe wherein the first probe hybridizes to a target region of SEQ. ID NO. 1 or a complementary strand thereof, and provides a detectable signal. Yet another embodiment of the invention encompasses a second probe, wherein the second probe hybridizes to a target region of SEQ. ID NO. 10 or a complementary strand thereof, and provides a detectable signal.

In a more particular embodiment, the first probe hybridizes to a target site corresponding to nucleotides 130 to 175 of SEQ. ID. NO. 1 or a complementary strand thereof. In another particular embodiment, the first probe hybridizes to a target site corresponding to nucleotides 135 to 170 of SEQ. ID. NO. 1 or a complementary strand thereof. In yet another particular embodiment, the first probe hybridizes to a target site corresponding to nucleotides 141 to 166 of SEQ. ID. NO. 1 or a complementary strand thereof.

In another particular embodiment, a second probe hybridizes to a target site corresponding to nucleotides 690 to 735 of SEQ ID NO 10 or a complementary strand thereof. In another particular embodiment, the second probe hybridizes to a target site corresponding to nucleotides 695 to 730 of SEQ. ID. NO. 10 or a complementary strand thereof. In yet another particular embodiment, the second probe hybridizes to a target site corresponding to nucleotides 703 to 724 of SEQ. ID. NO. 10 or a complementary strand thereof.

In another particular embodiment of the invention, the probes of the invention are oligonucleotide probes. In a more particular embodiment the probes comprise up to 50 nucleotides, preferably the probe is about 10-30 nucleotides long, and more preferably oligonucleotide probe is about 15-25 nucleotides long. In an even more particular embodiment the probe is of sequence SEQ ID. NO. 3 or sequence SEQ ID. NO. 6. In another particular embodiment, the probe is fluorescently labeled.

8.2.3.1. Labels

The labels attached to the probes of this invention comprise a set of energy or electron transfer moieties comprising at least one donor and at least one acceptor moiety. The label can be any type of differentiating label (e.g., a nucleic acid sequence that is not CSF-specific), a detectable molecule (e.g., a fluorescent group that can be inserted by known methods using, for example, fluorescein isothiocyanate), or digoxigenin, or a molecule that can be immobilized, such as biotin (by means of which the oligonucleotide can be bound to a streptavidin-coated surface, for instance).

Typically, the label will include a single donor moiety and a single acceptor moiety. Nevertheless, a label may contain more than one donor moiety and/or more than one acceptor moiety. For example, a set could comprise three moieties. Moiety one may be a donor fluorophore which, when exited and located in close proximity to moiety two, can then transfer energy to moiety two of the label. Thereafter, moiety two, which when excited and located in close proximity to moiety three, can transfer energy to moiety three of the label. Consequently, energy is transferred between all three moieties. In this set, moiety two is both an acceptor of energy from moiety one and a donor of energy to moiety three.

The donor and acceptor moieties operate such that one or more acceptor moieties accepts energy transferred from the one or more donor moieties or otherwise quench signal from the donor moiety or moieties. Transfer of energy may occur through collision of the closely associated moieties of a label (non-FRET) or through a nonradiative process such as fluorescence resonance energy transfer (FRET). For FRET to occur, transfer of energy between donor and acceptor moieties requires that the moieties be close in space and that the emission spectrum of a donor have substantial overlap with the absorption spectrum of the acceptor (See: Yaron et al. Analytical Biochemistry, 95, 228-235 (1979) and particularly page 232, col. 1 through page 234, col. 1). Alternatively, non-FRET energy transfer may occur between very closely associated donor and acceptor moieties whether or not the emission spectrum of a donor moiety has a substantial overlap with the absorption spectrum of the acceptor (See: Yaron et al. Analytical Biochemistry, 95, 228-235 (1979) and particularly page 229, col. 1 through page 232, col. 1). This process is referred to as intramolecular collision since it is believed that quenching is caused by the direct contact of the donor and acceptor moieties Preferred donor and acceptor moieties are fluorophore and quencher combinations, respectively. Numerous amine reactive labeling reagents are commercially available (as for example from Molecular Probes, Eugene, Oreg.). Preferred labeling reagents will be supplied as carboxylic acids or as the N-hydroxysuccinidyl esters of carboxylic acids. Preferred fluorochromes (fluorophores) include 5(6)-carboxyfluorescein (Flu), 6-((7-amino-4-methylcoumarin-3-acetyl)amino) hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine 2, 3, 3.5, 5 and 5.5 are available as NHS esters from Amersham, Arlington Heights, Ill.) or the Alexa dye series (Molecular Probes, Eugene, Oreg.). The most preferred fluorophores are the derivatives of fluorescein and particularly 5 and 6-carboxyfluorescein. The acceptor moiety may be a second fluorophore but preferably the acceptor moiety is a quencher moiety. A quencher moiety is a moiety which can quench detectable signal from a donor moiety such as a fluorophore. Most preferably, the quencher moiety is an aromatic or heteroaromatic moiety which is substituted with one or more azo or nitro groups. The most preferred quencher moiety is 4-((-4-(dimethylamino)phenyl)azo)benzoic acid (dabcyl).

8.2.4. Kits of the Invention

The invention also encompasses kits for detecting CSFV comprising primers according to the invention and separately packaged reagents for performing PCR. Such a kit preferably comprises at least one labelled oligonucleotide, wherein that labelled oligonucleotide detects CSFV in the region amplified by the primers. The oligonucleotide primers of the kit may be SEQ ID NO. 2, SEQ ID NO. 4, SEQ ID NO. 6 and SEQ ID NO. 7. The labelled oligonucleotide probes of the kit may be SEQ ID NO. 3, SEQ ID NO. 6, SEQ ID NO. 8, or SEQ ID NO. 9, wherein SEQ ID NO. 3 and SEQ ID NO. 6 would be labelled as desired.

Preferred kits of this invention comprise all the reagents to perform a PCR reaction wherein each of the labeled probes of the kit are used to monitor a sample for the presence, absence or quantity of CSFV. In preferred embodiments, one or more of the oligonucleotides of the kit perform as the primers in the PCR reaction.

A typical kit will contain at least two primers, at least one probe, nucleotide triphosphates, polymerase enzyme (preferably thermostable polymerase) and a buffer solution (with controlled ionic strength, controlled magnesium content and pH modulator).

9. EXAMPLES

A. Example 1

Viruses and Cells

Viruses used in this study (9× BDV, 22× BVDV 1, 19× BVDV 2, 36× CSFV, atypical *Pestivirus* Giraffe (Avalos et al., 2001), atypical *pestivirus* D32/00 “HoBi”[Schirrmeier et al., 2004]) are listed within the virus bank of the National Reference Laboratory for CSF located at the Friedrich-Loeffler-Institut, Insel Riems (Germany). Some of the isolates were obtained from the Community Reference Laboratory for CSF (TiHo Hannover, Germany). All CSFV strains were cultured using porcine kidney cells (PK-15), whereas the BDV and BVDV were propagated using bovine kidney cells (MDBK), or sheep thymus cells (SFT-R). The cell lines were provided by the Collection of Cell Lines in Veterinary medicine (CCLV), Insel Riems (Germany).

B. Example 2

Virus Isolation Using Cell Culture

Cell cultures were inoculated with different dilutions of the virus strains, and incubated at 37° C. After 4 days, the monolayers of the cells were heat-fixed, and stained with the *Pestivirus* specific monoclonal antibody C16 (Peters et al., 1986). All virus isolations were performed in duplicate. CSFV titers were determined using log10 dilution steps in quadruplicate. Virus titers were calculated as tissue culture infectious dosage 50% ($TCID_{50}$) per ml.

C. Example 3

RNA Isolation and Addition of an Internal Control

Viral RNA was extracted from cell culture using the QIAamp viral RNA kit (Qiagen) according to the manufacturers instructions, modified by addition of the internal control (IC) RNA. Briefly, 140 μl cell culture supernatant was added to 560 μl lysis buffer, vortexed and incubated at room temperature for 5 min. Subsequently, 5 μl in vitro transcribed IC RNA ($2\times10^5$ copies/μl) was added. After 5 min, 560 μl of ethanol was added and the solution was centrifuged through a QIAamp spin column. After washing the column twice with the appropriate buffer, the RNA was eluted using 50 μl elution buffer, and stored at −20° C.

D. Example 4

Primers, Probes, and TagMan® Real-Time RT-PCR

The Alignment of the different CSFV sequences was performed using the Genetics Computer Group software package (GCG Wisconsin). Alignment-based primer and probe selection was supported by the software package Beacon Designer 2.06 (PremierBiosoft). All oligonucleotides were synthesized by the MWG Biotech AG (Ebersberg, Germany) and stored at −20° C. until use. Table 1 shows the primers and probes used for the real-time RT-PCR assays of this report.

In order to minimize the risk of cross contaminations, a one-step RT-PCR protocol was chosen using the commercially available QuantiTect™ Probe RT-PCR kit (Qiagen). The real-time RT-PCR assay was optimised using a total volume of 25 μl. Briefly, for a single well 3.25 μl RNase-free water, 12.51 μl 2×QuantiTect Probe RT-PCR Master Mix, 0.25 μl QuantiTect Probe RT Mix, 2 μl CSF-specific primer-probe-mix (0.6 μM CSF-specific primers +0.1 μM CSF-specific probes) and 2 μl IC-specific primer-probe-mix (0.2 μM EGFP-specific primers +0.1 μM EGFP1-HEX probe) were pooled as a master mix, and finally 5 μl RNA template was added.

The real-time RT-PCR was carried out in an iCycler IQ™ Real-Time Detection System (BioRad) using the following temperature profile: 30 min at 50° C. (reverse transcription), 15 min at 95° C. (inactivation reverse transcriptase/activation Taq polymerase), followed by 42 cycles of 15 sec at 94° C. (denaturation), 30 sec at 57° C. (annealing) and 30 sec at 68° C. (elongation). The identical temperature profile was used for all real-time RT-PCR runs and fluorescence values were collected during the annealing step.

E. Example 5

In Vitro Transcription of Plasmid DNA

Linearised and gel purified plasmid DNAs were in vitro transcribed using the Riboprobe® System-SP6/T7 (Promega) according to the manufacturers instructions. The T7 transcribed positive control and the SP6 transcribed internal control were digested with the supplied DNase and purified using the RNeasy kit (Qiagen). The correct length of the transcribed RNAs was confirmed by formaldehyde agarose gel electrophoreses, and the concentration was determined by spectrophotometry. The exact number of RNA molecules was calculated using the formula: (X g/μl RNA/[transcript length in nucleotides×340])$\times6.022\times10^{23}$=Y molecules/μl.

Usually $10^{12}$ to $10^{13}$ RNA molecules were obtained in a 50 μl in vitro transcription procedure, enough for several thousand RT-PCR. The stock solutions of the in vitro-transcribed RNA was stored at −70° C., and the diluted working solutions were stored at −20° C.

F. Example 6

Design of a CSF-Specific Real-Time RT-PCR

In a first step, 78 sequences of the 5'NTR of different CSFV strains were aligned and a consensus sequence was calculated (FIG. 1). Only relevant wobble nucleotides, which were divergent in 4 or more of the compared CSFV strains (underlined in FIG. 1) were considered for the selection of primers and probes. Oligonucleotides with two relevant wobble nucleotides in the consensus sequence were only used, when both divergent nucleotides were not part of the 5'NTR of a single CSFV strain. In a second step, a CSFV-specific real-time RT-PCR system was designed, and named “CSF-System 1”. The “CSF-System 1” consists of the primer pair CSF100-F/CSF192-R, and the FAM-labelled probe CSF-Probe 1 (FIG. 1, Table 1), and amplifies a fragment of 93 bp between nt 100 and 192 of the 5'-NTR of CSFV (strain Alfort 187 [Accession No. X87939]; FIG. 1).

Both primers and the probe of “CSF-System 1” were titrated in chequerboard assays to identify the most suitable concentrations, which were defined as the maximal fluorescence values combined with the earliest threshold cycle. For the “CSF-System 1” 0.6 μM/reaction of the primers and 0.1 μM/reaction of the probe were identified as an optimum for the detection of CSFV genomes.

G. Example 7

Construction of a Positive and an Internal Control Plasmid

Using the primers CSF100-F and CSF383-R (Table 1), a 284 bp fragment of the 5'-NTR of CSFV Alfort/187 (Accession No. X87939) was amplified by RT-PCR, purified and inserted into the standard cloning vector pGEM-Teasy (Promega). The obtained plasmid pGEM-PC3alf (FIG. 2) was used for the in vitro transcription of the positive control (PC)RNA. The internal control (IC) plasmid was similarly constructed. Using the primer EGFP1-F and EGFP2-R (Table 1), a 132 bp fragment of the pEGFP-1 standard vector (BD Bioscience Clontech) was amplified by PCR and cloned into the pGEM-Teasy cloning vector (FIG. 2). The resulting IC plasmid was named pGEM-EGFP 1. Both plasmids were controlled by sequencing with the M13 standard primer. The CSFV 5'-NTR fragment in pGEM-PCalf was ligated in forward orientation, whereby the EGFP fragment had been inserted in reverse orientation into pGEM-EGFP 1.

H. Example 8

Analytical Sensitivity Of "CSF-System 1"

The analytical sensitivity of "CSF-System 1" was determined with a dilution series of the in vitro-transcribed PC-RNA. In a first 10-fold dilution series of the in vitro-transcribed PC-RNA it was ascertained that the "CSF-System 1" amplified the PC in a linear manner from $10^1$ copies/well up to $10^9$ copies/well with a PCR Efficiency of 99.8% (FIGS. 3*a* and *b*). In a more detailed analysis, the specific analytical sensitivity limit of the assay was determined using a 2-fold dilution series of the PC-RNA. Finally, a detection limit of about 8 copies/well for the single "CSF-System 1" assay was detected (Table 2).

I. Example 9

Design of an EGFP-Specific Real-Time RT-PCR for Amplification and Detection of an Internal Control For the internal control of each sample or sample pool concerning both RNA isolation and RT-PCR, a heterologous IC-RNA real-time RT-PCR assay was designed. The in vitro transcribed IC could be added to each sample either before RNA isolation or before RT-PCR, and was amplified with a EGFP-specific real-time RT-PCR system, which was named "IC-System 1." The 132 bp amplicon of primer pair EGFP 1-F/EGFP 2-R was detected using the HEX-labelled probe EGFP 1-HEX (Table 1). In chequerboard assays the concentrations for both primers and the probe were titrated and the analytical sensitivity of the "IC-System 1" was analysed using dilution series of the in vitro-transcribed IC-RNA. Finally, a sensitivity limit of the IC assay between 10 and 100 copies/well was determined (data not shown).

For a maximal sensitivity of the CSFV-specific real-time RT-PCR system it was necessary to limit the primers of "IC-System 1". The minimal concentration of primers which amplified the EGFP fragment without a significant increase of the threshold cycle were determined for the fine-tuning of multiplex real-time RT-PCR assays. Finally, 0.2 μM/reaction of the EGFP forward and reverse primers and 0.1 μM/reaction of the probe were used for the IC detection in multiplex assays.

J. Example 10

Combination of "CSF-System 1" and "IC-System 1" in a Multiplex Real-Time RT-PCR Assay After determination of the primer and probe concentrations in an optimal single CSF-specific real-time RT-PCR assay, and identification of limited concentrations for the IC-specific primers, an optimised multiplex CSF-specific real-time RT-PCR protocol was established. Therefore, the analytical sensitivities of the single and the multiplex real-time RT-PCR assays were compared. Firstly, batches of a 2 fold dilution series of the PC-RNA were amplified with or without co-amplification of the IC-RNA. Starting with 1000 copies PC-RNA per RT-PCR well, an identical sensitivity limit of 8 copies per RT-PCR reaction for the single as well as for the multiplex assay could be detected (Table 4). Secondly, dilution series of extracted CSFV-RNA were amplified with or without co-amplification of the IC. In these experiments, similar results were generated for both systems. As an example, fluorescence signals following amplification of a dilution series of RNA of CSFV strain "Paderborn" (genotype 2.1.) are shown in FIG. 3*a*. Black lines illustrate the FAM-fluorescence values of the single assay, while the grey lines with squares show the FAM-fluorescence values of the multiplex assay including co-amplification of the IC. Amplification of the internal control (IC) is separately depicted in FIG. 3*b*. It has to be mentioned that all RT-PCR reactions with a co-amplification of the IC showed detectable HEX fluorescence signals, and the amount of IC-RNA was adjusted to reach threshold cycles (TC) of approximately 30. The observed range of TCs for the IC in the multiplex assay was between 29 and 32 (FIG. 3*b*), and TC scores of the IC were the higher the higher the copy number of CSFV genomes has been in the test (FIG. 3*b*). Nevertheless, a competitive inhibition of the IC amplification, caused by the favoured amplification of larger quantities of CSFV-RNA, was observed (FIG. 3*b*).

K. Example 11

Sensitivity of the Multiplex "CSF-System 1" Compared to the "Gold Standard" Virus Isolation For a comparative study of "CSF-System 1" with the "gold standard" virus isolation, 10 fold dilution series of CSFV positive cell culture supernatants were prepared (Table 2). One aliquot of each dilution series was used for virus isolation, a second aliquot was used for RNA isolation and multiplex real-time RT-PCR analysis. Several strains of different CSFV genotypes were included in the investigation, and the results clearly demonstrated the high sensitivity of the multiplex real-time RT-PCR assay. In most cases, the sensitivity of the real-time RT-PCR assay was at least identical (CSFV-Uelzen, genotype 2.3) or even higher (CSFV-Kozlov, genotype 1.2; CSFV-Paderborn, genotype 2.1) than virus isolation (Table 3). However, in the case of the cell culture adapted strain Alfort 187 (genotype 1.1), sensitivity of the real-time RT-PCR was approximately 10-fold reduced in comparison to the virus isolation (Table 3).

L. Example 12

Specificity of the CSF-Real-Time RT-PCR Assays

In order to estimate the ability of the multiplex assay to distinguish CSFV from BVDV, BDV, or atypical *pestiviruses* a panel of 90 different *pestivirus* strains was tested (Table 3). All 36 different CSFV strains, members of all known CSFV genotypes, were correctly detected (Table 3), and furthermore, a scarped curve progression of the fluorescence signals was observed in all cases (data not shown). Even in the case of the CSFV strain "Kanagawa", a genotype 3.4 CSFV, no marked differences of the TC values and fluorescence signals were observed (data not shown). The specificity of the real-time RT-PCR assay was also proven with serum samples (n=100) from a defined negative pig population. RNA was isolated from the samples and tested in the multiplex CSFV-specific real-time RT-PCR. All samples scored negative and only background fluorescence levels were observe).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All cited patents, patent applications and publications referred to in this application are herein incorporated by reference in their entirety.

TABLE 1

Primer and probes used in this study

| Name | Sequence 5' → 3' | Genome position [a] |
|---|---|---|
| CSF 100-F | ATG CCC AYA GTA GGA CTA GCA | 100-120 |
| CSF-Probe 1 | FAM-TGG CGA GCT CCC TGG GTG GTC TAA GT-TAMRA | 141-166 |
| CSF 192-R | CTA CTG ACG ACT GTC CTG TAC | 192-172 |
| EGFP 1-F | GAC CAC TAC CAG CAG AAC AC | 637-656 |
| EGFP 1-HEX | HEX-AGC ACC CAG TCC GCC CTG AGC A-BHQ1 | 703-724 |
| EGFP 2-R | GAA CTC CAG CAG GAC CAT G | 768-750 |

[a] Genome position according to CSFV Alfort/187 (accession number: X87939) and standard cloning vector pEGFP-1 (BD Bioscience Clontech, accession number: U55761), respectively.

TABLE 2

Sensitivity of the real-time RT-PCR assay compared to the virus isolation

| CSFV strain (genotype) | Dilution | Virus isolation 1. Titration | 2. Titration | RT-PCR CSF-System1 |
|---|---|---|---|---|
| Alfort (1.1) | $10^{-1}$ | 4/4 | 4/4 | + |
| | $10^{-2}$ | 4/4 | 4/4 | + |
| | $10^{-3}$ | 4/4 | 4/4 | + |
| | $10^{-4}$ | 4/4 | 4/4 | + |
| | $10^{-5}$ | 4/4 | 4/4 | + |
| | $10^{-6}$ | 4/4 | 2/4 | – |
| | $10^{-7}$ | 0/4 | 2/4 | – |
| | $10^{-8}$ | 0/4 | 0/4 | – |
| | | TCID$_{50}$: $10^{6.5}$/0.1 ml | | |
| Kozlov (1.2) | $10^{-1}$ | 4/4 | 4/4 | + |
| | $10^{-2}$ | 0/4 | 1/4 | + |
| | $10^{-3}$ | 0/4 | 0/4 | + |
| | $10^{-4}$ | 0/4 | 0/4 | – |
| | $10^{-5}$ | 0/4 | 0/4 | n.d. |
| | $10^{-6}$ | 0/4 | 0/4 | n.d. |
| | $10^{-7}$ | 0/4 | 0/4 | n.d. |
| | $10^{-8}$ | 0/4 | 0/4 | n.d. |
| | | TCID$_{50}$: $10^{1.75}$/0.1 ml | | |
| Paderborn (2.1) | $10^{-1}$ | 4/4 | 4/4 | + |
| | $10^{-2}$ | 4/4 | 4/4 | + |
| | $10^{-3}$ | 4/4 | 4/4 | + |
| | $10^{-4}$ | 4/4 | 3/4 | + |
| | $10^{-5}$ | 0/4 | 0/4 | + |
| | $10^{-6}$ | 0/4 | 0/4 | – |
| | $10^{-7}$ | 0/4 | 0/4 | n.d. |
| | $10^{-8}$ | 0/4 | 0/4 | n.d. |
| | | TCID$_{50}$: $10^{4.25}$/0.1 ml | | |
| Uelzen (2.3) | $10^{-1}$ | 4/4 | 4/4 | + |
| | $10^{-2}$ | 4/4 | 4/4 | + |
| | $10^{-3}$ | 4/4 | 4/4 | + |
| | $10^{-4}$ | 3/4 | 4/4 | + |
| | $10^{-5}$ | 1/4 | 0/4 | + |

TABLE 2-continued

Sensitivity of the real-time RT-PCR assay compared to the virus isolation

| CSFV strain (genotype) | Dilution | Virus isolation 1. Titration | 2. Titration | RT-PCR CSF-System1 |
|---|---|---|---|---|
| | $10^{-6}$ | 0/4 | 0/4 | – |
| | $10^{-7}$ | 0/4 | 0/4 | n.d. |
| | $10^{-8}$ | 0/4 | 0/4 | n.d. |
| | | TCID$_{50}$: $10^{4.5}$/0.1 ml | | |

n.d. = not dedicated

TABLE 3

Specificity of the real-time RT-PCR assay

| Pestiviruses | Genotype | Number of strains | CSF-System 1 |
|---|---|---|---|
| CSFV | 1.1 | 7 | +++ |
| | 1.2 | 4 | +++ |
| | 2.1 | 6 | +++ |
| | 2.2 | 5 | +++ |
| | 2.3 | 12 | +++ |
| | 3.1 | 1 | +++ |
| | 3.4 | 1 | +++ |
| | | Σ36 | |
| BDV | | 9 | – |
| BVDV | I | 22 | – |
| | II | 19 | – |
| | atypical | 4 | – |
| | | Σ45 | |

TABLE 4

Sensitivity of the real-time RT-PCR assay compared with and without co-amplification of the internal control (IC)

| T7-PC3alf (Copies/well) | CSF-System 1 Without IC-Amplification | With IC-Amplification |
|---|---|---|
| 1000 | + | + |
| 800 | + | + |
| 600 | + | + |
| 400 | + | + |
| 200 | + | + |
| 100 | + | + |
| 80 | + | + |
| 60 | + | + |
| 40 | + | + |
| 20 | + | + |
| 10 | + | + |
| 8 | + | + |
| 6 | – | – |
| 4 | – | – |
| 2 | – | – |

What is claimed is:

1. A method for detecting the presence of classical swine fever virus (CSFV) ribonucleic acids in a biological sample, said method comprising:

(i) obtaining a biological sample, said biological sample comprising ribonucleic acids;

(ii) reverse transcribing said ribonucleic acids to obtain cDNA;

(iii) contacting said cDNA with a first forward primer, a first reverse primer, and a DNA polymerase to produce a first PCR product, wherein the first forward primer consists of SEQ ID NO: 2, and the first reverse primer consists of SEQ ID NO: 4;

(iv) hybridizing to the first PCR product a first nucleic acid probe consisting of SEQ ID NO: 3;

(v) contacting an internal control ribonucleic acid derived from SEQ ID NO: 10 with a second forward primer and a second reverse primer to produce a second PCR product, wherein the second forward primer hybridizes to a target site corresponding to nucleotides of SEQ ID NO: 10 or a complementary strand thereof, and the second reverse primer hybridizes to a target site corresponding to nucleotides of SEQ ID NO: 10 or a complementary strand thereof;

(vi) hybridizing to the second PCR product a second nucleic acid probe that hybridizes to a target site corresponding to nucleotides of SEQ ID NO: 10 or a complementary strand thereof; and (vii) detecting hybridization of said first nucleic acid probe to said first PCR product, wherein hybridization of said first nucleic acid probe to said first PCR product is indicative of the presence of CSFV nucleic acids in the biological sample.

2. The method of claim 1, wherein the second forward primer hybridizes to a target site corresponding to nucleotides 625 to 675 of SEQ ID NO: 10 or a complementary strand thereof.

3. The method of claim 2, wherein the second forward primer hybridizes to a target site corresponding to nucleotides 630 to 665 of SEQ ID NO: 10 or a complementary strand thereof.

4. The method of claim 3, wherein the second forward primer hybridizes to a target site corresponding to nucleotides 637 to 656 of SEQ ID NO: 10 or a complementary strand thereof.

5. The method of claim 1, wherein the second reverse primer hybridizes to a target site corresponding to nucleotides 740 to 780 of SEQ ID NO: 10 or a complementary strand thereof.

6. The method of claim 5, wherein the second reverse primer hybridizes to a target site corresponding to nucleotides 745 to 775 of SEQ ID NO: 10 or a complementary strand thereof.

7. The method of claim 6, wherein the second reverse primer hybridizes to a target site corresponding to nucleotides 750 to 768 of SEQ ID NO: 10 or a complementary strand thereof.

8. The method of claim 1, wherein the second probe hybridizes to a target site corresponding to nucleotides 690 to 635 of SEQ ID NO: 10 or a complementary strand thereof.

9. The method of claim 8, wherein the second probe hybridizes to a target site corresponding to nucleotides 695 to 730 of SEQ ID NO: 10 or a complementary strand thereof.

10. The method of claim 9, wherein the second probe hybridizes to a target site corresponding to nucleotides 703 to 724 of SEQ ID NO: 10 or a complementary strand thereof.

11. A method for detecting the presence of classical swine fever virus (CSFV) ribonucleic acids in a biological sample, said method comprising:

(i) reverse transcribing ribonucleic acids obtained from the biological sample to obtain cDNA;

(ii) contacting said cDNA with a first forward primer, a first reverse primer, and a DNA polymerase to produce a first PCR product, wherein the first forward primer consists of SEQ ID NO: 2, and the first reverse primer consists of SEQ ID NO: 4;

(iii) hybridizing to the first PCR product a first nucleic acid probe consisting of SEQ ID NO: 3;

(v) contacting an internal control ribonucleic acid derived from SEQ ID NO: 10 with at least two second primers capable of hybridizing to the internal control ribonucleic acid; and (iv) detecting hybridization of said first nucleic acid probe to said first PCR product, wherein hybridization of said first nucleic acid probe to said first PCR product is indicative of the presence of CSFV nucleic acids in the biological sample.

12. The method of claim 11, wherein one of the at least two second primers is a second forward primer.

13. The method of claim 12, wherein the second forward primer hybridizes to a target site corresponding to nucleotides 625 to 675 of SEQ ID NO: 10 or a complementary strand thereof.

14. The method of claim 13, wherein the second forward primer hybridizes to a target site corresponding to nucleotides 630 to 665 of SEQ ID NO: 10 or a complementary strand thereof.

15. The method of claim 14, wherein the second forward primer hybridizes to a target site corresponding to nucleotides 637 to 656 of SEQ ID NO: 10 or a complementary strand thereof.

16. The method of claim 11, wherein one of the at least two second primers is a second reverse primer.

17. The method of claim 16, wherein the second reverse primer hybridizes to a target site corresponding to nucleotides 740 to 780 of SEQ ID NO: 10 or a complementary strand thereof.

18. The method of claim 17, wherein the second reverse primer hybridizes to a target site corresponding to nucleotides 745 to 775 of SEQ ID NO: 10 or a complementary strand thereof.

19. The method of claim 18, wherein the second reverse primer hybridizes to a target site corresponding to nucleotides 750 to 768 of SEQ ID NO: 10 or a complementary strand thereof.

20. The method of claim 11 further comprising contacting said internal control ribonucleic acid with a second nucleic acid probe.

21. The method of claim 20, wherein the second probe hybridizes to a target site corresponding to nucleotides 690 to 635 of SEQ ID NO: 10 or a complementary strand thereof.

22. The method of claim 21, wherein the second probe hybridizes to a target site corresponding to nucleotides 695 to 730 of SEQ ID NO: 10 or a complementary strand thereof.

23. The method of claim 22, wherein the second probe hybridizes to a target site corresponding to nucleotides 703 to 724 of SEQ ID NO: 10 or a complementary strand thereof.

24. A method for detecting the presence of classical swine fever virus (CSFV) ribonucleic acids in a biological sample, said method comprising:

(i) obtaining a biological sample, said biological sample comprising ribonucleic acids;

(ii) reverse transcribing said ribonucleic acids to obtain cDNA;

(iii) contacting said cDNA with a first forward primer, a first reverse primer, and a DNA polymerase to produce a first PCR product, wherein the first forward primer consists of SEQ ID NO: 2, and the first reverse primer consists of SEQ ID NO: 4;

(iv) hybridizing to the first PCR product a first nucleic acid probe consisting of SEQ ID NO: 3;

(v) contacting an internal control ribonucleic acid derived from SEQ ID NO: 10 with a second forward primer and a second reverse primer to produce a second PCR product, wherein the second forward primer hybridizes to a target site corresponding to nucleotides 637 to 656 of SEQ ID NO: 10 or a complementary strand thereof, and the second reverse primer hybridizes to a target site corresponding to nucleotides 750 to 768 of SEQ ID NO: 10 or a complementary strand thereof;

(vi) hybridizing to the second PCR product a second nucleic acid probe that hybridizes to a target site corresponding to nucleotides 703 to 724 of SEQ ID NO: 10 or a complementary strand thereof; and (vii) detecting hybridization of said first nucleic acid probe to said first PCR product, wherein hybridization of said first nucleic acid probe to said first PCR product is indicative of the presence of CSFV nucleic acids in the biological sample.

25. The method of claim 1 or 24, where said second nucleic acid probe is an oligonucleotide probe.

26. The method of claim 25, wherein said second nucleic acid probe comprises 50 nucleotides.

27. The method of claim 25, wherein said second nucleic acid probe is about 10 to 30 nucleotides long.

28. The method of claim 27, wherein said second nucleic acid probe is about 15 to 25 nucleotides long.

29. The method of claim 1, or 24, wherein the detecting is measuring a change in fluorescence.

30. The method of claim 25, wherein the first and/or second probe is fluorescently labeled.

31. The method of claim 1 or 24, wherein said second forward and second reverse primers comprise 50 nucleotides.

32. The method of claim 1 or 24, wherein said second forward and second reverse primers are about 10 to 30 nucleotides long.

33. The method of claim 32, wherein said second forward and second reverse primers are about 10 to 30 nucleotides long.

34. A method of quantifying classical swine fever virus (CSFV) viral load in a first isolated sample, comprising:

(i) contacting said first isolated sample with a first forward primer, a first reverse primer, and a DNA polymerase to produce a first PCR product, wherein the first forward primer consists of SEQ ID NO: 2, and the first reverse primer consists of SEQ ID NO: 4, and hybridizing a first nucleic acid probe consisting of SEQ ID NO: 3 to the first PCR product, wherein hybridizing the first nucleic acid probe consisting of SEQ ID NO: 3 to the first PCR product provides a first detectable signal, and measuring the intensity of said first detectable signal;

(ii) contacting said first sample with a second nucleic acid probe, wherein the second probe hybridizes to an internal control ribonucleic acid derived from SEQ ID NO: 10, wherein hybridization of the second nucleic acid probe to the internal control ribonucleic acid derived from SEQ ID NO: 10 provides a second detectable signal, and measuring the intensity of said second detectable signal;

(iii) contacting a control sample having a known CSFV viral load with a nucleic acid probe consisting of SEQ ID NO: 3 to provide a third detectable signal and measuring the intensity of said third signal; and (iv) comparing the intensity of the first signal to the intensity of the second signal and the third signal, wherein said comparing indicates the quantity of classical swine fever virus viral load in the first isolated sample.

35. The method of claim 1 or 24 wherein the CSFV nucleic acids are detected in a closed tube format either in real time or at an assay end-point.

36. The method of claim 1 or 24, further comprising analysis of a CSFV nucleic acid positive control, wherein the analysis of a CSFV nucleic acid positive control is comprised of contacting a nucleotide sequence fragment derived from SEQ ID NO: 11 with the first forward primer, the first reverse primer, and a DNA polymerase to produce a positive control PCR product, hybridizing the first nucleic acid probe to the positive control PCR product, and detecting hybridization of said first nucleic acid probe to said positive control PCR product.

* * * * *

UNITED STATES PATENT AND TRADEMARK OFFICE

CERTIFICATE OF CORRECTION

PATENT NO. : 7,608,433 B2
APPLICATION NO. : 11/052762
DATED : October 27, 2009
INVENTOR(S) : Bernd Hoffmann et al.

It is certified that error appears in the above-identified patent and that said Letters Patent is hereby corrected as shown below:

Column 42, line 59, Claim 33

In claim 33, delete “10 to 30” and insert --15 to 25--, therefor.

Signed and Sealed this
Fifth Day of March, 2013

Teresa Stanek Rea
*Acting Director of the United States Patent and Trademark Office*